(12) United States Patent
Brown et al.

(10) Patent No.: US 6,402,736 B1
(45) Date of Patent: Jun. 11, 2002

(54) APPARATUS AND METHOD FOR FILTERING INTRAVASCULAR FLUIDS AND FOR DELIVERING DIAGNOSTIC AND THERAPEUTIC AGENTS

(76) Inventors: Joe E. Brown, 1900 Glenn Club Dr., #1106, Stone Mountain, GA (US) 30087; Matt D. Pursley, 430 Cameron Woods Ct., Alpharetta, GA (US) 30202

(*) Notice: Subject to any disclaimer, the term of this patent is extended or adjusted under 35 U.S.C. 154(b) by 0 days.

(21) Appl. No.: 09/558,078

(22) Filed: Apr. 25, 2000

Related U.S. Application Data

(63) Continuation-in-part of application No. 09/168,133, filed on Oct. 7, 1998, now Pat. No. 6,053,900, and a continuation-in-part of application No. PCT/US98/02770, filed on Feb. 13, 1998, which is a continuation-in-part of application No. 08/801,576, filed on Feb. 14, 1997, now abandoned, which is a continuation-in-part of application No. 08/602,424, filed on Feb. 16, 1996, now Pat. No. 5,603,694.
(60) Provisional application No. 60/088,152, filed on Jun. 5, 1998.

(51) Int. Cl.[7] .............................................. A61M 25/00
(52) U.S. Cl. ........................ 604/523; 604/264; 604/500
(58) Field of Search .................................. 604/500, 501, 604/502, 506, 530, 507, 527, 508, 523, 525, 526; 606/200, 159

(56) References Cited

U.S. PATENT DOCUMENTS

| | | | |
|---|---|---|---|
| 4,650,466 A | * | 3/1987 | Luther .......................... 604/95 |
| 5,256,146 A | | 10/1993 | Ensminger et al. |
| 5,523,092 A | * | 6/1996 | Hanson et al. .............. 424/423 |

FOREIGN PATENT DOCUMENTS

WO     WO 95/20416     8/1995

* cited by examiner

Primary Examiner—Manuel Mendez
(74) Attorney, Agent, or Firm—Jeffrey L. Thompson; Thompson & Thompson, P.A.

(57) ABSTRACT

An apparatus and method for filtering intravascular fluids and for delivering diagnostic and therapeutic agents intravascularly is disclosed in which the apparatus has a shape defined by a preset shape of a resilient fiber core. The resilient fiber core is covered by a soft polymer tubing or other polymer material to form a delivery apparatus that takes the shape of the resilient fiber core. Various shapes and structures are disclosed that infuse diagnostic and therapeutic agents through a lumen of the polymer tubing, that deliver the agents in the form of a soluble coating, that circulate or contain a preloaded charge of radioactive material for intravascular radiotherapy, and that deploy filtration devices intravascularly for removing particulate matter from body fluid. The resilient fiber core and soft polymer material permit the construction of a very small apparatus that can be removed easily following treatment. Various deployment systems are disclosed for deploying the filtering and delivery apparatuses into a vessel and for protecting against radiation exposure.

19 Claims, 32 Drawing Sheets

FIG. 4
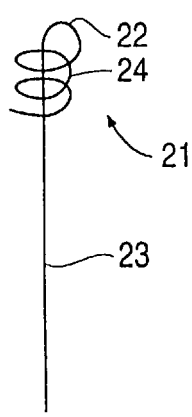
FIG. 5
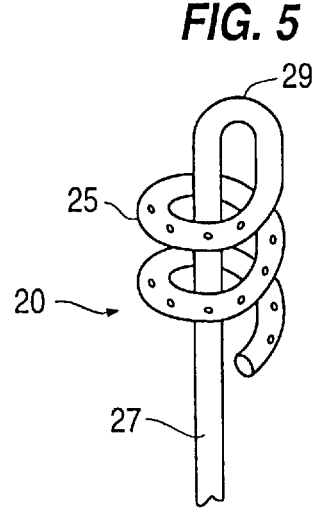
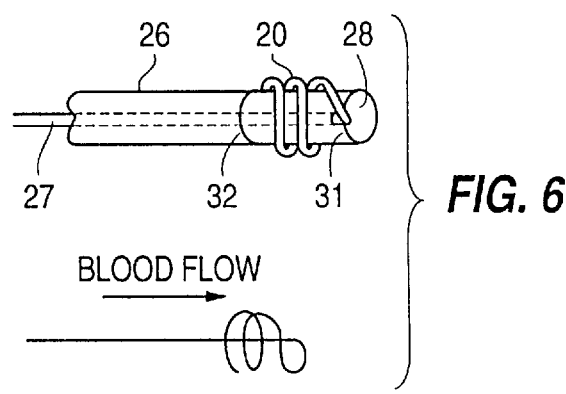
BLOOD FLOW
FIG. 6
FIG. 7
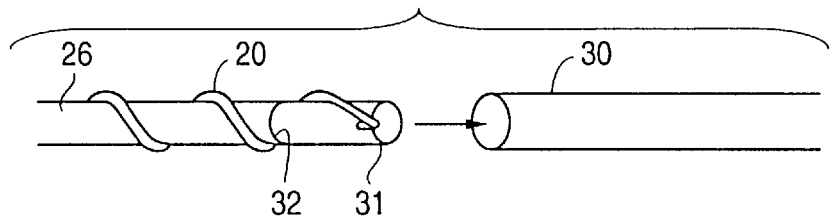
FIG. 8
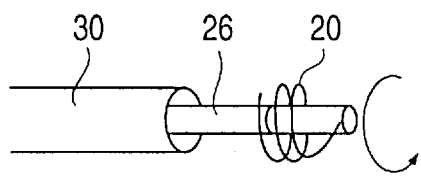

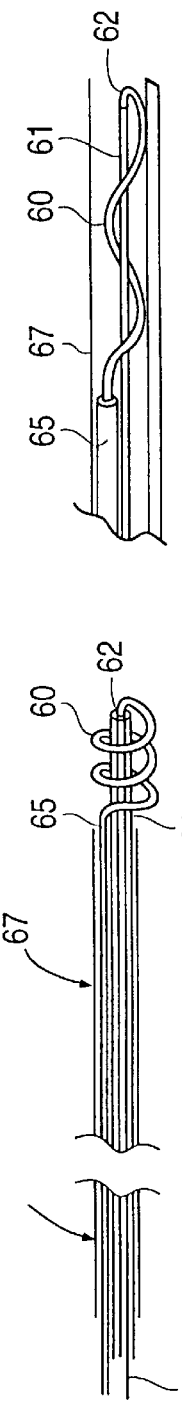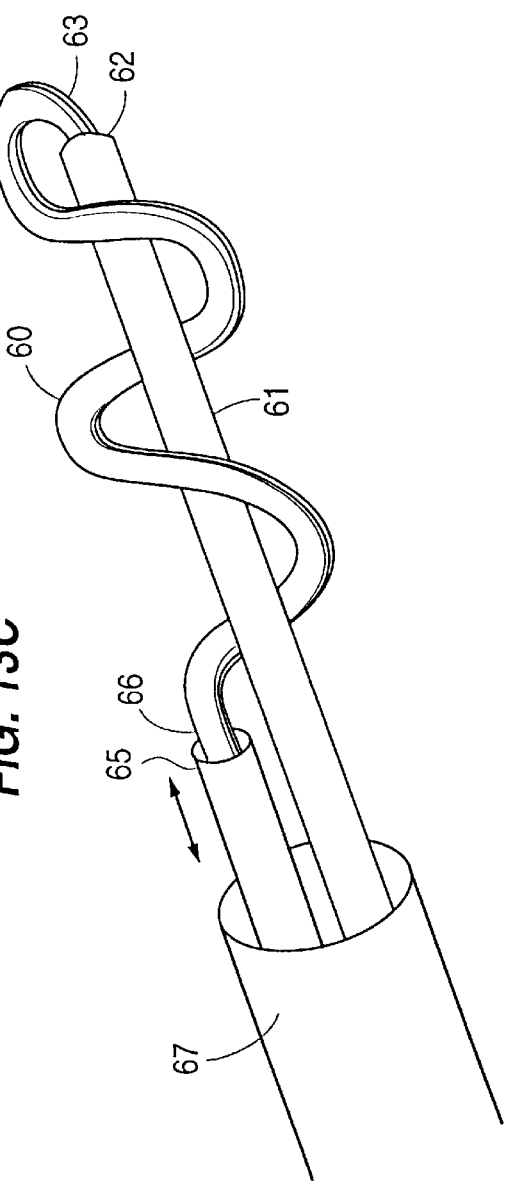
FIG. 13A
FIG. 13B
FIG. 13C

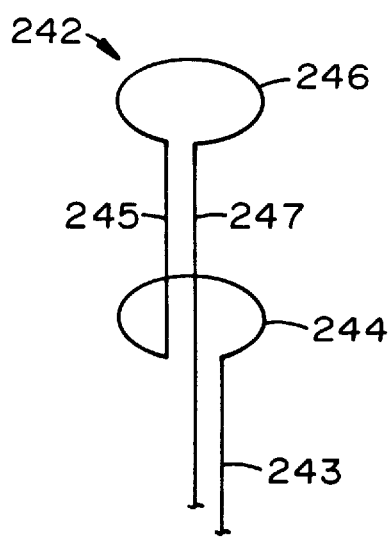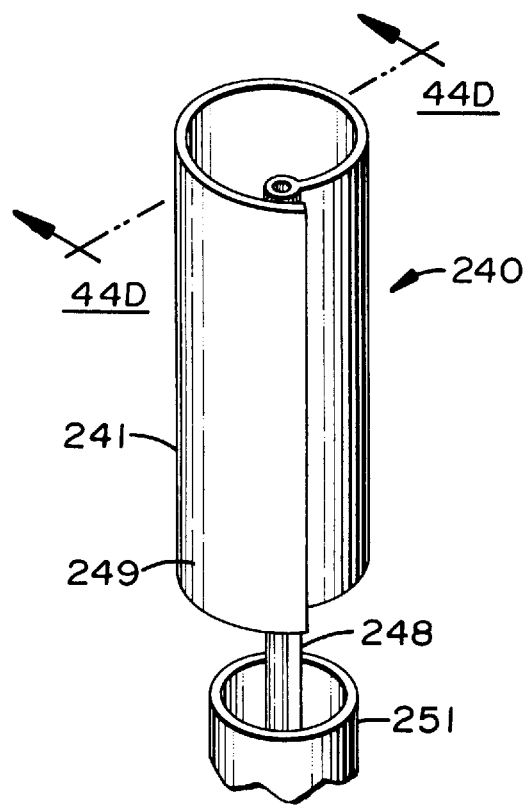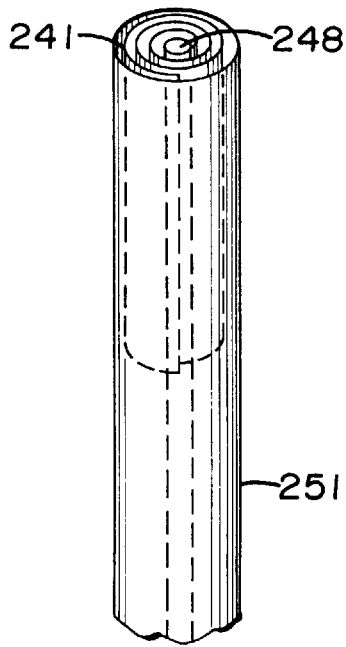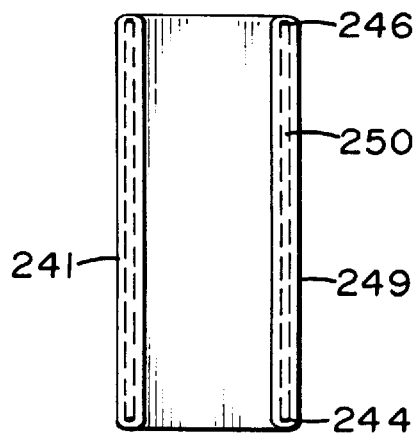
FIG. 44A
FIG. 44B
FIG. 44C
FIG. 44D

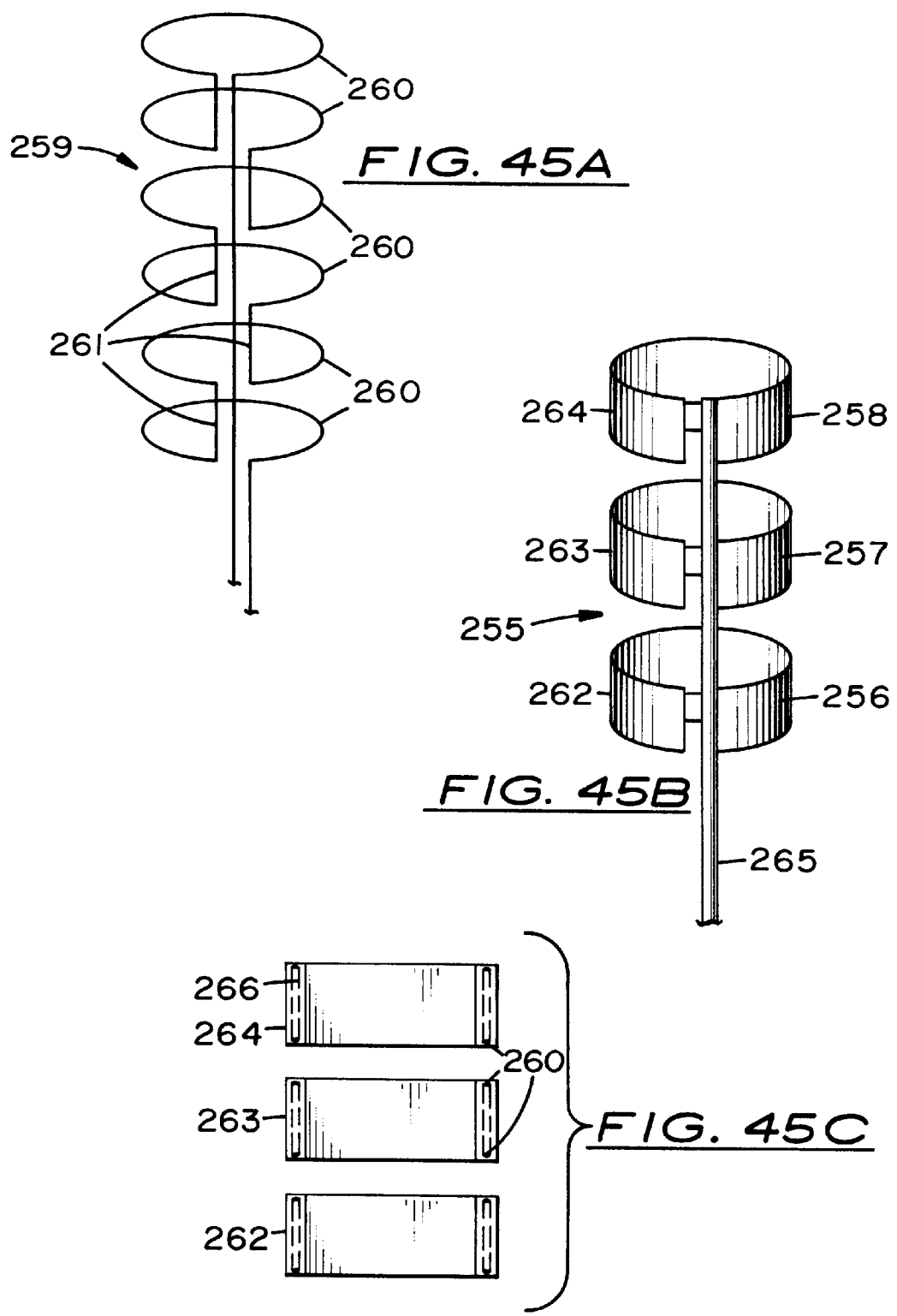

APPARATUS AND METHOD FOR FILTERING INTRAVASCULAR FLUIDS AND FOR DELIVERING DIAGNOSTIC AND THERAPEUTIC AGENTS

RELATED APPLICATIONS

This application is a continuation-in-part of applicants' U.S. application Ser. No. 09/168,133, filed on Oct. 7, 1998, now U.S. Pat. No. 6,053,900, which claims the benefit of U.S. Provisional Application Serial No. 60/088,152 filed on Jun. 5, 1998, and is a continuation-in-part of Applicants' copending International Application No. PCT/US98/02770 filed Feb. 13, 1998, which is a continuation-in-part of Applicants' U.S. application Serial No. 08/801,576, filed on Feb. 14, 1997, now abandoned, which is a continuation-in-part of applicants' U.S. application Ser. No. 08/602,424, filed Feb. 16, 1996, now U.S. Pat. No. 5,603,694. These contents of these prior applications are incorporated herein by reference.

BACKGROUND OF THE INVENTION

1. Field of the Invention

The present invention relates generally to apparatuses and methods for filtering intravascular fluids and for delivering diagnostic and therapeutic agents into a living organism. The invention includes embodiments of various shapes and structures that are used to infuse therapeutic agents or deliver such agents intravascularly in the form of a soluble coating, and other embodiments that circulate or contain a preloaded charge of radioactive material for intravascular radiotherapy. The invention further includes embodiments for filtering intravascular fluids using filtration devices placed within the living organism.

2. Description of the Related Art

Atherosclerosis is a cardiovascular disease in which deposits of plaques (atheromas) containing cholesterol, lipid material, foam cells, lipophages and proliferating smooth muscle cells are within the intima and media of large to small diameter arteries such as the aorta and the iliac, femoral, coronary and cerebral arteries. The resultant stenosis causes a reduction in blood flow.

Attempts to treat atherosclerosis have included bypass surgery wherein the diseased vascular segments are augmented by prosthetic or natural grafts. This procedure requires general anesthesia and a substantial healing period after surgery and, thus, is generally limited to cases of severe coronary artery disease.

Other approaches for the recanalization of stenotic vessels include percutaneous transluminal coronary angioplasty (PTCA), atherectomy, stenting and newer modalities of cardiovascular intervention, including laser angioplasty. The primary drawbacks of these procedures has been the appearance of restenosis at or near the site of the original stenosis in the blood vessel that requires a secondary angioplasty procedure or a bypass surgery. Another occurrence that reduces the success of a typical angioplasty procedure is that frequently the stenotic plaque or intima of the blood vessel or both are dissected during the angioplasty procedure by the inflation of the balloon. Upon the deflation of the balloon, a section of the dissected lining (commonly termed "flap") will collapse into the bloodstream, thereby closing or significantly reducing the blood flow through the vessel. In these instances, emergency bypass surgery is often required to avoid a myocardial infarct distal to the blockage.

In recent years, various devices and methods (other than bypass surgery) for prevention of restenosis and for repairing damaged blood vessels have become known. These methods typically use an expandable cage or region (commonly termed "stent") on the distal end of a catheter designed to hold a detached lining against an arterial wall for extended periods to facilitate the reattachment thereof. Some stents are designed for permanent implantation inside the blood vessel, and others are designed for temporary use inside the vessel.

Typically, the expandable region of the prior art stents is formed by a braided wire or balloon attached to the distal end of the catheter body. Such designs are difficult and expensive to manufacture, and create reliability concerns due to the existence of high stress points located at the connection of the braided wire region with the catheter body and at the connections between the intermingled wire strands.

Alternatively, or in addition to the use of stents, various drugs have been applied to the site of the dilated lesion to prevent or reduce chances of restenosis and to aid in the healing of flaps, dissection or other hemorrhagic conditions that may appear after an angioplasty procedure. The prior art braided wire and balloon stents, as disclosed, for example, in U.S. Pat. Nos. 4,655,771, 5,295,962, 5,368,566 and 5,421,826, cannot be used to deliver or inject fluid-based agents to the specific site of the lesion while maintaining adequate flow in the vascular lumen. The fluid flow through the lumen is substantially blocked by these stents during use.

In recognition of this problem, temporary stenting catheters with drug delivery capabilities have been developed, as disclosed, for example, in U.S. Pat. Nos. 5,383,928 and 5,415,637. The '928 patent discloses a coil-shaped stent covered by a polymer sheath for local drug delivery. A drug is incorporated into the polymer sheath for controlled release of the drug upon insertion. Because the polymer sheath itself is as large as the diameter of the coil, the device cannot be removed from the subject outside of the lab and without a guiding catheter. Moreover, the device is limited in its ability to adapt to the shape and size of the vessel wall, and in that only drugs that are compatible with and can be incorporated into the polymer can be delivered by the device.

The temporary stenting catheter of the '637 patent functions to hold a collapsed dissected lining or flap against the blood vessel wall for a sufficient time to allow the natural adhesion of the flap to the blood vessel wall. The stenting catheter of the '637 patent also functions to introduce a drug to the site of the vascular procedure to aid in the adhesion process and in the prevention of restenosis while allowing the flow of blood through the vessel to locations distal to the catheter.

The catheter assembly of the '637 patent, however, has a number of disadvantages. The catheter assembly is complex and expensive to manufacture. More importantly, however, the catheter assembly of the '637 is very expensive to use because it requires a guiding catheter to be maintained within the vessel and the patient to be maintained within the catheter lab during use and deployment.

There are other known devices, as disclosed, for example, in U.S. Pat. Nos. 4,531,933, 4,694,838, 4,813,925, 4,887, 996, and 5,163,928, that use a catheter having a heat set polymer stent at a distal end shaped as a halo or coil. These devices require pushing a rod through the lumen of the heat set curve in the polymer to straighten the device so that it may be inserted into the body through a guide catheter. The rod is then removed and the curve shape of the catheter comes back. These devices suffer from being limited in size due to the fact that a relatively large wire must be used to straighten the device (e.g., 0.014" to 0.016"). Thus, the lumen size of these devices are correspondingly large. The devices also suffer from a lack of ability to be deformed (i.e., coiled, bent, or shaped) without permanent deformation. Because of the permanent deformation, the devices fail to track the inside of a vessel that is not round.

The prior art drug delivery systems cannot be left in place for a period of time outside the lab in which the angioplasty was performed, and then removed by a nurse by simply pulling the system out. Any coil that relies on a balloon for its intravascular shape requires inflation to maintain the coil's shape, and the patient is required to stay in the lab under fluoro to make sure the coil stays in place. Any coil that relies on the modules of the polymer to maintain the coil shape is too rigid to pull out and requires the use of a straightening rod to push through the coil so that the coil straightens out before removal. This procedure would not be permitted outside the catheter lab, thus, adding significant cost to the procedure.

Another method of preventing or controlling restenosis following angioplasty has been developed in recent years which uses intravascular radiotherapy (IRT). IRT may also be used to prevent stenosis following cardiovascular graft procedures or other trauma to the vessel wall. IRT involves introducing a radioactive material, such as a beta emitting material (for example, $^{32}P$) or a photon emitting material (for example, $^{125}I$), into a blood vessel for a predetermined time to provide a radiation dosage. The radiation dosage must be carefully controlled to impair or arrest hyperplasia without causing excessive damage to healthy tissue. Overdosing of a section of blood vessel can cause arterial necrosis, inflammation and hemorrhaging, while under dosing will result in no inhibition of smooth muscle cell hyperplasia, or even exacerbation of the hyperplasia and resulting restenosis.

An IRT method using a radioactive stent is disclosed in U.S. Pat. No. 5,059,166. The radioactive stent is designed to be permanently implanted in the blood vessel after completion of a lumen opening procedure. The radiation dose delivered to the patient is determined by the activity of the stent at the particular time it is implanted.

Another IRT method is disclosed in U.S. Pat. No. 5,302, 168, which uses a radioactive source contained in a flexible carrier with remotely manipulated windows. This method generally requires the use of a higher activity source than the radioactive stent to deliver an effective dose to the patient. Accordingly, measures must be taken to ensure that the source is maintained at the center of the lumen to prevent localized overexposure of tissue to the radiation source. Use of a higher activity source also requires expensive shielding and other equipment for safe handling. Conventional IRT methods also tend to block or restrict blood flow through the vessel during treatment.

Thus, there is a need for an improved system and method for delivering diagnostic and therapeutic agents intravascularly that overcomes the problems of the existing systems. There is also a need for an improved system and method for filtering intravascular fluids with filtration devices that can be deployed and removed efficiently and without blocking fluid flow through the vessel during treatment.

SUMMARY OF THE INVENTION

It is an object of the present invention to provide a method and system for delivering diagnostic and therapeutic agents intravascularly that overcomes the problems in the above-mentioned prior art.

It is a further object of the present invention to provide a delivery system for delivering diagnostic and therapeutic agents with an extremely soft coil shape for engaging a vessel.

It is a further object of the present invention to provide a delivery system for diagnostic and therapeutic agents that can be removed from the body without the use of guiding catheters or introduction devices, and that can be left in place for a period of time outside the lab where it was installed and removed by simply pulling it out.

It is a further object of the present invention to provide a delivery system for diagnostic and therapeutic agents that is very small and flexible, and that has an improved ability to track the inside of a vessel and to be deformed (i.e., coiled, bent, or shaped) without permanent deformation.

It is a further object of the present invention to provide a coil-shaped delivery system with the above advantages that has a radiopaque polymer tubing or radiopaque coating over a polymer tubing for observation under a fluoroscope or other X-ray device.

It is a further object of the present invention to provide a coil-shaped delivery system having multiple lumens for delivering fluid-based agents and/or withdrawing fluid samples.

It is a further object of the present invention to provide a coil-shaped delivery system having a number of different shapes to suit a particular application.

It is a further object of the present invention to provide a coil-shaped delivery system having an inner sheath to guide diagnostic and therapeutic agents to a wall of a vessel.

It is yet a further object of the present invention to provide a coil-shaped delivery system having a soluble coating on the surface of a coil that dissolves when placed in a body fluid in a vessel.

It is a still further object of the present invention to provide a coil-shaped delivery system that can be deployed by introducing a pressure through the lumen of the coil that causes the coil to unwind and expand in diameter against the wall of the vessel.

It is a still further object of the present invention to provide a coil-shaped delivery system that has telescoping, concentric support tubes connected to respective ends of the coil that can be manipulated in a push-pull or twist manner to change the diameter and length of the coil to provide precise deployment.

It is a further object of the present invention to provide an apparatus shaped by a resilient fiber core and having a return line or vent tube for introducing or circulating a suspension of radioactive material within a vessel to provide intravascular radiotherapy.

It is a still further object of the present invention to provide an apparatus shaped by a resilient fiber core and preloaded with a radioactive material for use in intravascular radiotherapy.

It is a still further object of the present invention to provide a system for intravascular radiotherapy including an apparatus preloaded with a radioactive material and a protective container for transporting the preloaded apparatus to minimize handling and exposure of radioactive components by the user.

It is a still further object of the present invention to provide a system for filtering fluids intravascularly that can be deployed and removed easily and efficiently without blocking a flow of fluid through the vessel, and that can be used to introduce therapeutic agents upstream or downstream of the filtration structure.

Additional objects, advantages, and novel features of the invention will be set forth in the following description, and will become apparent to those skilled in the art upon reading this description or practicing the invention. The objects and advantages of the invention may be realized and attained by the appended claims.

To achieve the foregoing and other objects and in accordance with the purpose of the present invention, as embodied and broadly described herein, the coil apparatus of the present invention comprises a resilient fiber core having a linear portion and a coiled portion, and a polymer tubing encasing the resilient fiber core and adapting to the shape of the resilient fiber core, the polymer tubing comprising a first portion encasing the linear portion of the resilient fiber core and a second portion encasing the coiled portion of the resilient fiber core.

In one embodiment, the polymer tubing has a lumen extending along a length of the polymer tubing, and the second portion of the polymer tubing comprises means for releasing a fluid-based agent delivered through the lumen from the coil apparatus. The releasing means may comprise a series of openings spaced along the second portion of the polymer tubing, or a porous, braided, or stitched material of the polymer tubing.

The polymer tubing may comprise multiple lumens for delivering fluid-based agents and/or withdrawing fluid samples. Moreover, an inner sheath may be secured to the polymer tubing to guide fluid-based agents to a wall of a vessel in which the coil is deployed.

In an alternative arrangement, an outer surface of the coiled portion of the polymer tubing is covered with a soluble coating containing a therapeutic agent. The soluble coating is then dissolved when the coil is placed in a body fluid contained in a vessel. In another arrangement, a first portion of the polymer tubing is covered with a soluble coating containing a therapeutic agent, and a second portion of the polymer tubing has a releasing means for delivering fluid-based agents from a lumen of the polymer tubing.

In another embodiment, the apparatus is formed with a vent tube or return passage for allowing a suspension of radioactive material to be introduced and/or circulated through a portion of the polymer tubing after it is deployed in a vessel. A polymer tubing with a return passage can be formed using a double lumen tubing having distal ends of the lumens connected together, or by using a single lumen tubing having both ends of the coiled portion connected to respective linear portions of the tubing. Alternatively, a vent tube can be inserted into a lumen of a polymer tubing to permit a radioactive suspension to be introduced into the lumen while air is being vented out of the lumen. A deployment sheath formed of a high density material or having a high density liner is provided to protect the vessel from incidental radiation when the apparatus is being deployed in or removed from the vessel.

In another embodiment, a radioactive material is preloaded into the apparatus to minimize handling and exposure of radioactive components by the user. The preloaded apparatus is then loaded into a deployment sheath and placed in a protective container formed of a high density material or with a lead liner to prevent radiation exposure during shipping and handling before and after the apparatus is deployed in a vessel for treatment. The preloaded apparatus can have a wider variety of shapes and structures since there is no need for a supply or return passage.

In yet another embodiment, the portion of the device preloaded with a radioactive material is formed as a separate member from rest of the device and is connected to the device before deployment using a suitable fitting. The portion of the device containing the radioactive material can then be kept in a separate protective container from the rest of the device, thus facilitating handling of the radioactive components.

The radioactive material can be in the form of a liquid suspension, a powder, encapsulated balls, or the like placed within the coiled portion. Alternatively, the coiled portion can be exposed to a radiation source for a predetermined time to make the wire core or another material preloaded into the device radioactive.

With the construction of the present invention, the apparatus can be extremely small. For example, the resilient fiber core can be formed of a metallic steel heat-tempered spring alloy, such as a titanium-nickel-chromium alloy, or a boron fiber having a diameter of 0.001 to 0.006 inches. The polymer tubing can have an outside diameter of 0.003 to 0.014 inches and an inside diameter of 0.002 to 0.008 inches. The polymer tubing is preferably formed of a very soft material, such as nylon, urethane, PE and TFE polymer materials, and has a Shore D hardness of approximately 40 so as to minimize resistance to the preformed shape of the resilient fiber core and prevent damage to a vessel during use. The polymer tubing is constructed of a polymer compounded with a radio opacifier at a loading high enough to make the polymer radiopaque.

In a first embodiment, the coiled portion of the resilient fiber core is shaped into a forward feed coil shape extending away from the linear portion of the resilient fiber core.

In a second embodiment, the resilient fiber core is shaped into a reverse feed coil shape with a bent transition portion between the linear portion and the coiled portion, the bent transition portion directing the coiled portion in a reverse direction back along the linear portion.

In additional embodiments, the coiled portion of the resilient fiber core is shaped into a forward feed coil shape extending away from the linear portion of the resilient fiber core and includes a distal end portion that can be engaged by a catheter for deployment purposes.

The resilient fiber core may also be pre-shaped in a number of different shapes to suit a particular application. For example, the resilient fiber core may be spiral-shaped in plan view, or helical-shaped with a tapered diameter.

In a further aspect of the present invention, in accordance with its objects and purposes, the present invention comprises a combination of a coil apparatus for delivering diagnostic and therapeutic agents intravascularly and an apparatus for deploying the coil apparatus at a desired location in a vessel, the coil apparatus comprising a resilient fiber core having a linear portion and a coiled portion, and a polymer tubing encasing the resilient fiber core and adapting to the shape of the resilient fiber core, the polymer tubing comprising a first portion encasing the linear portion of the resilient fiber core and a second portion encasing the coiled portion of the resilient fiber core.

The apparatus for deploying the coil apparatus comprises a delivery sheath, the delivery sheath having an inside diameter that is smaller than a preset diameter of the coiled portion for compressing the coil apparatus during deployment.

In one embodiment, the apparatus for deploying the coil apparatus further comprises a push tube for pushing the coil apparatus out of the delivery sheath during deployment, the push tube being slidable over a linear portion of the coil apparatus.

In another embodiment, the apparatus for deploying the coil apparatus further comprises a deployment catheter that is slidable over the coil apparatus, the deployment catheter comprising a slotted distal end for receiving the bent transition portion of the coil apparatus to permit pushing and twisting of the coil apparatus during deployment.

In other embodiments, the apparatus for deploying the coil apparatus further comprises a deployment catheter having a means for holding the distal end portion to permit pushing and twisting of the coil apparatus during deployment. The holding means may comprise a notch and snare or other suitable holding structure across a distal end of the deployment catheter for receiving and holding the distal end portion of the infusion coil apparatus. Alternatively, the holding means may utilize a friction lock formed in the distal end of the deployment catheter into which the distal end portion of the infusion coil apparatus can be inserted and securely held during deployment.

In another embodiment, a first marker is provided at a forward distal end of the deployment catheter and a second marker is spaced axially rearwardly from the first marker. The first and second markers are radiopaque for determining placement of the infusion coil apparatus within a vessel. The first and second markers are spaced apart a distance equal to an axial length of the coiled portion in a relaxed position of the coiled portion.

According to another embodiment of the present invention, the deployment apparatus is further provided with a proximal holding tube positioned over a linear portion of the infusion coil. The proximal holding tube has a distal end abutting a coiled portion of the infusion coil and is secured to the infusion coil. The proximal holding tube permits manipulation of the infusion coil during deployment using the proximal holding tube in conjunction with the deployment catheter.

In another embodiment of the present invention, the delivery sheath of the deployment apparatus further comprises a guide tube extending from a point adjacent a distal end of the delivery sheath to an opening in a side wall of the delivery sheath. The guide tube is secured to the side wall of the delivery sheath and has an inner diameter large enough to permit a guide wire to pass therethrough.

In a further aspect of the present invention, in accordance with its objects and purposes, the present invention comprises a method for delivering diagnostic and therapeutic agents into a vessel, comprising the steps of providing an infusion coil apparatus having a resilient fiber core encased by a soft polymer tubing, loading the infusion coil apparatus into a delivery sheath, the delivery sheath having an internal diameter which is smaller than a preset diameter of a coiled portion of the resilient fiber core, inserting the delivery sheath and the infusion coil apparatus into a vessel, and pushing the infusion coil apparatus out of the delivery sheath whereby the resilient fiber core causes the infusion coil apparatus to increase in diameter and lodge in the vessel. The method further comprises the step of feeding a fluid-based agent through the polymer tubing of the infusion coil apparatus into the vessel, or the step of covering an outer surface of the coiled portion of the polymer tubing with a soluble coating containing a therapeutic agent.

In one embodiment of the present invention, the method further comprises the steps of sliding a push tube over a linear portion of the infusion coil apparatus, pushing the infusion coil apparatus out of the delivery sheath using the push tube, and removing the push tube and the delivery sheath from the vessel while maintaining the infusion coil apparatus within the vessel.

In another embodiment of the present invention, the method further comprises the steps of providing the infusion coil apparatus with a reverse feed coil shape with a bent transition portion between a linear portion and a coiled portion, the bent transition portion directing the coiled portion in a reverse direction back along the linear portion, providing a deployment catheter having a slotted distal end, sliding the deployment catheter over the infusion coil apparatus and receiving the bent transition portion of the infusion coil apparatus in the slotted distal end of the deployment catheter.

In other embodiments of the present invention, the method further comprises the steps of providing the infusion coil apparatus with a forward feed coil shape extending away from a linear portion of the resilient fiber core, and a distal end portion, providing a deployment catheter having a holding structure in a distal end of the deployment catheter, and receiving and securing the distal end portion of the infusion coil apparatus in the holding structure of the deployment catheter.

The method may further comprise the steps of pushing the infusion coil apparatus out of the delivery sheath into the vessel with the deployment catheter, and twisting the deployment catheter to rewind the infusion coil apparatus into a deployed position against a wall of the vessel. The method also may include the steps of providing first and second radiopaque marks on the deployment catheter, the first and second marks being spaced apart a distance approximately equal to an axial length of the coiled portion in a relaxed position of the infusion coil apparatus, and twisting the deployment catheter to rewind the infusion coil apparatus until the axial length of the coiled portion is approximately the same as the distance between the first and second marks.

In another embodiment of the present invention, the method for delivering diagnostic and therapeutic agents further comprises the steps of providing the infusion coil apparatus with a forward feed coil shape extending away from a linear portion of the resilient fiber core, providing a proximal holding tube over a linear portion of the infusion coil, the proximal holding tube having a distal end abutting a coiled portion of the infusion coil, the proximal holding tube being secured to the infusion coil, sliding the proximal holding tube and the deployment catheter in opposite directions to elongate and reduce the diameter of a coiled portion of the infusion coil apparatus, placing the elongated coil into the delivery sheath, pushing the infusion coil apparatus out of the delivery sheath into the vessel using the deployment catheter and the proximal holding tube, and sliding the proximal holding tube and the deployment catheter in opposite directions to compress and increase the diameter of the coiled portion of the infusion coil apparatus, whereby the infusion coil apparatus is placed in a deployed position against a wall of the vessel.

In another embodiment of the present invention, the method further comprises the steps of providing a guide tube within the delivery sheath, the guide tube having a first distal end adjacent to a distal end of the delivery sheath, and a second proximal end in communication with an opening through a side wall of the delivery sheath, and sliding the guide tube over a guide wire to facilitate the step of inserting the delivery sheath and the infusion coil apparatus into a vessel.

In another embodiment of the present invention, a coil apparatus is deployed by placing a coiled portion of the apparatus in a vessel to be treated, and introducing a pressure into the lumen of the coiled portion to cause the coiled portion to unwind and expand in diameter within the vessel.

In yet another embodiment of the present invention, a precise deployment method is provided using a pair of telescoping, concentric support tubes connected to respective ends of the coiled portion of the apparatus, and manipulating the concentric support tubes to change the length and/or diameter of the coiled portion.

BRIEF DESCRIPTION OF THE DRAWINGS

The present invention will become more clearly appreciated as the disclosure of the present invention is made with reference to the accompanying drawings. In the drawings:

FIG. 3A shows the infusion coil in a loaded position. FIG. 3B shows the infusion coil in a deployed position within an artery wall. FIG. 3C shows the removal of the deployment mechanism.

FIG. 4 is a perspective view of a resilient fiber in an alternate coil shape according to a second embodiment of the present invention.

FIG. 5 is a perspective view of an infusion coil assembly according to the second embodiment.

FIGS. 6 to 8 illustrate the steps and mechanism for deploying the infusion coil of the second embodiment. FIG. 6 shows the infusion coil in a relaxed position on a deployment catheter.

FIG. 7 shows the infusion coil in a stretched position on the deployment catheter during insertion into a guide catheter.

FIG. 8 shows the torquing of the deployment catheter to rewind the infusion coil.

FIGS. 13A to 13C illustrate an infusion coil and deployment apparatus according to a fifth embodiment of the present invention. FIG. 13A shows the infusion coil in a shortened, radially enlarged position. FIG. 13B shows the infusion coil in an elongated, radially reduced position. FIG. 13C shows a perspective view of the infusion coil and deployment apparatus.

FIGS. 44A, 44B, 44C and 44D illustrate an apparatus having a flap portion preloaded with a radioactive material, wherein FIG. 44A shows a resilient fiber core for defining the shape of the apparatus; FIG. 44B shows the apparatus with a polymer material placed over the resilient fiber core; FIG. 44C shows the apparatus with the flap portion wound around the linear portion and contained within a deployment sheath; and FIG. 44D is a sectional view taken along line 44D—44D in FIG. 44B showing a space within the flap portion of the apparatus containing a radioactive material.

FIGS. 45A, 45B and 45C illustrate an apparatus having multiple flap portions preloaded with a radioactive material, wherein FIG. 45A shows a resilient fiber core for defining the shape of the apparatus; FIG. 45B shows the apparatus with a polymer material placed over the resilient fiber core; and FIG. 45C is a sectional view showing a space within the flap portions of the apparatus containing a radioactive material.

FIGS. 46A and 46B illustrate an apparatus having multiple ring portions preloaded with a radioactive material, wherein FIG. 46A is a perspective view of the apparatus; and FIG. 46B is a sectional view of the multiple ring portions taken along line 46B—46B in FIG. 46A.

FIGS. 47A and 47B illustrate another apparatus having multiple ring portions preloaded with a radioactive material, wherein FIG. 47A is a perspective view of the apparatus; and FIG. 47B is a sectional view of the multiple ring portions taken along line 47B—47B in FIG. 47A.

FIGS. 48A and 48B illustrate another shape for an apparatus preloaded with a radioactive material, wherein FIG. 48A shows a plurality of folded end segments at an end portion of the apparatus; and FIG. 48B shows the folded end segments formed into a generally cylindrical shape for deployment into a vessel.

DETAILED DESCRIPTION OF THE PREFERRED EMBODIMENTS

A first embodiment of the present invention will be described in detail hereinafter with reference to FIGS. 1, 2, and 3A to 3C.

Figure 1:
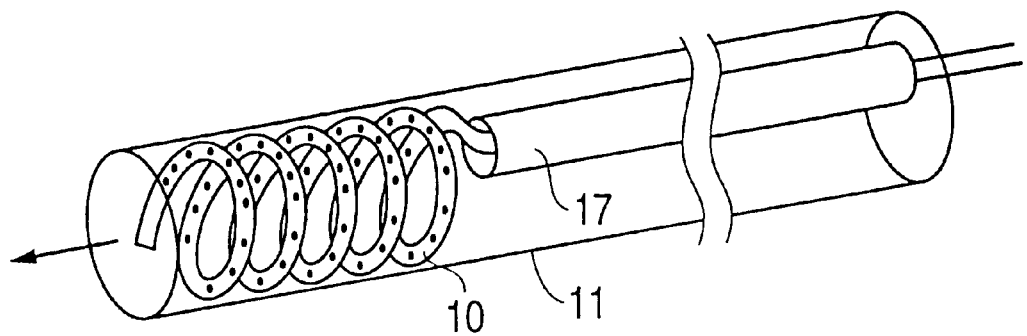
FIG. 1 is a perspective view of an infusion coil assembly according to a first embodiment of the present invention.
Figure 2:
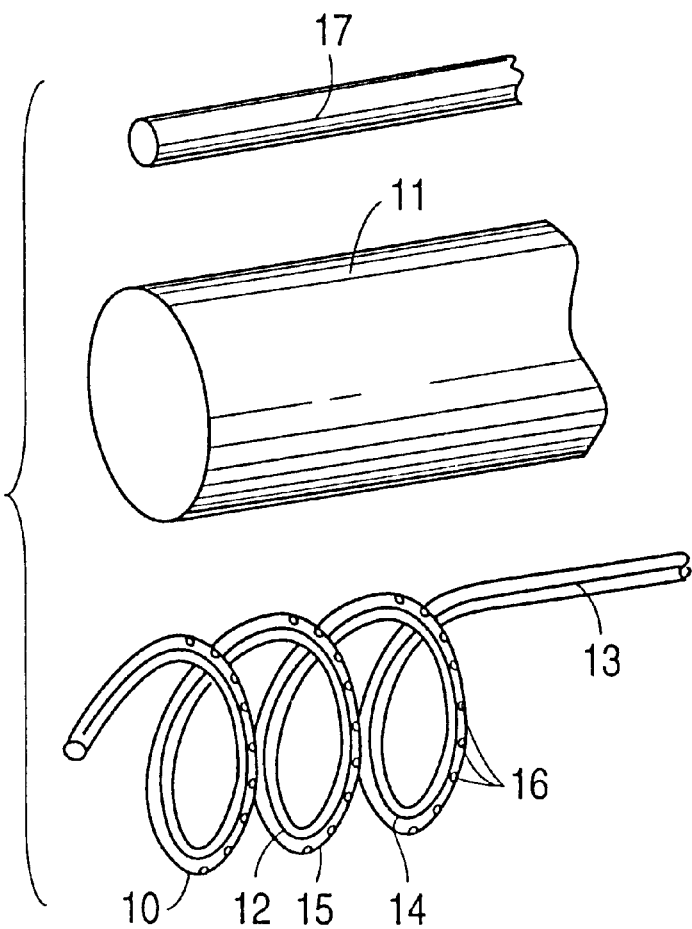
FIG. 2 is an exploded perspective view of the components shown in FIG. 1.
Figure 3A:
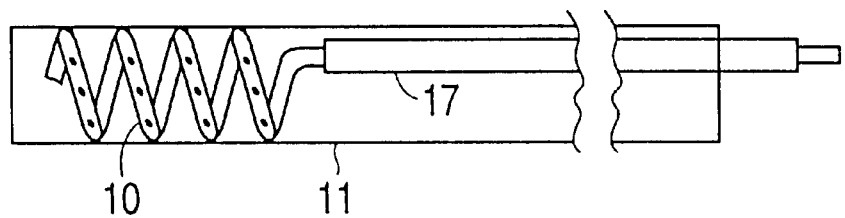
FIGS. 3A to 3C illustrate the steps and mechanism for deploying the infusion coil of the first embodiment.
Figure 3B:
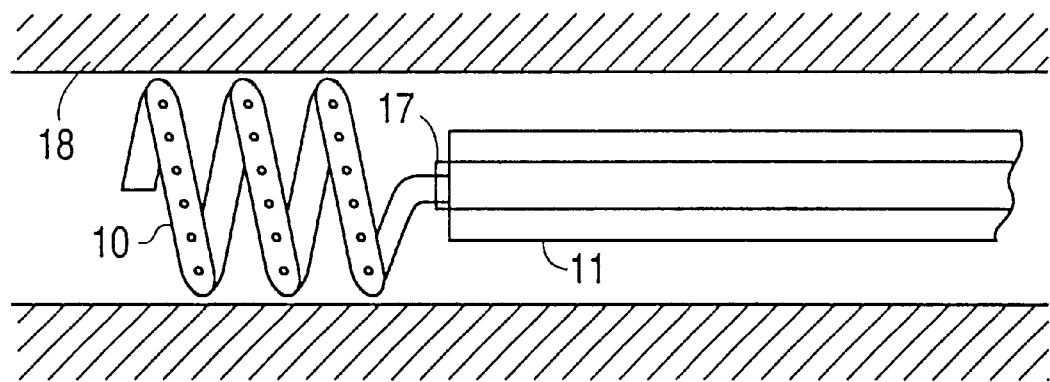
Figure 3C:
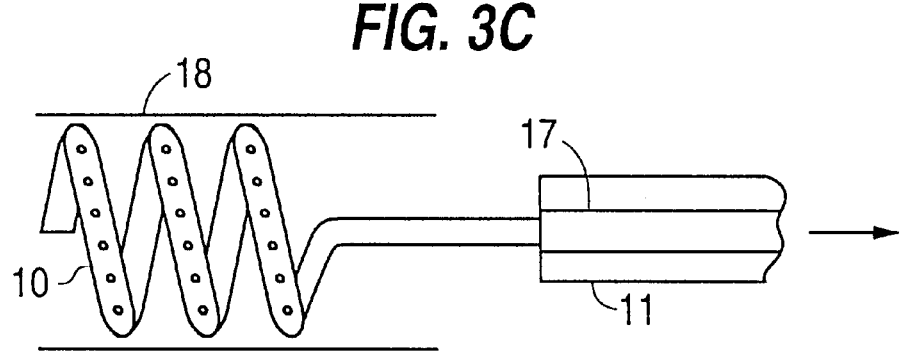

Referring to FIG. 1, an infusion coil 10 according to the first embodiment is shown in a loaded configuration (i.e., prior to deployment) in a delivery sheath 11 for deployment into a vessel of a subject. The infusion coil 10 includes a pre-shaped resilient fiber core 12, as seen in the exploded view of FIG. 2. The resilient fiber core 12 has a first linear portion 13 and a second coiled portion 14. The coiled portion 14 is formed at an end of the device for insertion into a vessel. The resilient fiber core 12 is encased by a soft, radiopaque polymer tubing 15 that adapts to the shape of the resilient fiber core 12, including the coiled portion 14. The resilient fiber core 12 extends through the lumen of the soft polymer tubing 15.

The preshape of the coiled portion 14 of the resilient fiber core 12 is a coil configuration with an outer diameter of the coil chosen so that it is slightly larger than the vessel in which the infusion coil 10 will be deployed. The combination of the resilient fiber core 12 and the soft polymer tubing 15 permit the infusion coil 10 to be wound into a much tighter coil than coils for delivering diagnostic and therapeutic agents of the prior art.

The soft polymer tubing 15 includes a series of holes 16 therein spaced along the circumference of the coil shape. The holes 16 provide an outlet for fluid-based agents injected through the tubing 15. The holes 16 in the tubing 15 may be formed by drilling, lasing, machining, punching, and so forth. Slots can be used in the coil of the tubing 15 instead of holes. In addition, the coiled portion of the tubing 15 can be constructed of porous materials such as PTFE and PVDF, or the end of the tubing can be braided, stitched, and so forth.

In operation, the infusion coil 10 in its loaded position (FIGS. 1 and 3A) is inserted into the body and directed to the desired site through an appropriate guiding catheter and/or guide wire. The device can be inserted directly over a guide wire already in place, as further explained below. The axial length of the device is minimized because the infusion coil 10 is in compression during deployment.

After reaching the desired location (FIG. 3B), a push tube 17 is used to push the infusion coil 10 out of the delivery sheath 11. As the infusion coil 10 exits the sheath 11, the resilient fiber core 12 springs back to its preset condition and lodges the infusion coil 10 in a vessel 18. The push tube 17 is fed directly over the linear portion of the infusion coil to provide positive attachment to the coil 10 for pushing and to prevent accidental over-extension of the push tube 17 into the vessel 18. After the infusion coil 10 is pushed completely out of the delivery sheath 11, the push tube 17 and delivery sheath 11 can be removed (FIG. 3C) leaving the infusion coil 10 in the vessel 18 by itself.

The polymer tubing 15 over the resilient fiber core 12 serves to cushion the impact of the infusion coil 10 onto the wall of the vessel 18 and provides a path for infusion of diagnostic and therapeutic diagnostic and therapeutic agents. The holes 16 placed around the entire periphery of the polymer tube 15 in the coil section permit antithrombotic fluid-based agents to be introduced over the entire circumference of the infusion coil 10 to prevent blood clotting problems associated with the deployment of similar devices.

The following dimensions and specific materials of the components of the delivery system are given by way of example only. The delivery sheath 11 can be formed of polymer (nylon) or fluoropolymer tube (teflon) having an outside diameter of 0.066" and an inside diameter of 0.058". The push tube 17 can be formed of a polymer tube (nylon) with or without a wire reinforcement. The push tube 17 can have an outside diameter of 0.032" and an inside diameter of 0.018".

The resilient fiber core 12 of the infusion coil 10 can be formed of a metallic steel heat-tempered spring alloy, such as a titanium-nickel-chromium alloy, a boron fiber, or other suitable resilient material. The resilient fiber core preferably has a diameter of 0.002" to 0.006". The polymer tubing 15 can be formed of a nylon, urethane, PE or TFE polymer material having an outside diameter of 0.012" to 0.014" and an inside diameter of 0.006" to 0.008". The polymer tubing 15 of the coil 10 is preferably very soft so that it offers virtually no resistance to the coiled portion 14 of the preformed resilient fiber core 12. This allows the resilient fiber core 12 to have a diameter as small as 0.002" and still maintain enough springback in the coil assembly to be lodged within a vessel 18. This is a crucial aspect of the device in that it is soft enough to prevent damage to the walls of the vessel 18 as it is inserted and removed.

Referring to FIGS. 4 to 8, a second embodiment of the present invention will be described. In the second embodiment, an infusion coil 20 is formed using a resilient fiber core 21 that is preshaped into a reverse feed coil shape, as shown in FIG. 4. Specifically, a bent transition portion 22 between a linear portion 23 of the resilient fiber core 21 and a coiled portion 24 of the resilient fiber core 21 directs the coiled portion 24 in a reverse direction back along the linear portion 23, rather than forward away from the linear portion, as in the embodiment of FIG. 1.

A polymer tubing 25 is then slid over the resilient fiber core 21, as in the first embodiment, and the infusion coil 20 takes the shape of the resilient fiber core 21, as shown in FIG. 5.

Referring to FIGS. 6 to 8, the steps and mechanism for deploying the infusion coil 20 of the second embodiment will be described. FIG. 6 shows the infusion coil 20 in a relaxed position on a deployment catheter 26. The deployment catheter 26 is slid over a linear portion 27 of the infusion tube 20. The deployment catheter 26 includes a slotted distal end 28 for receiving a portion of the infusion coil 20 at or near the transition portion 29 to permit pushing and twisting of the infusion coil 20 during deployment.

As shown in FIG. 7, the infusion coil 20 is pushed through a standard introduction device 30 for deployment, such as a guide catheter (i.e., delivery sheath) or a guide wire. The infusion coil 20 elongates into a stretched position when inserted into these devices because the coil 20 has a much larger relaxed diameter (e.g., 2.5 mm to 6 mm) than the passage diameter of the guide catheter or other delivery devices 30 (e.g., 1.5 mm to 2.5 mm). Once at the desired deployment location, the deployment catheter 26 is pushed and twisted to force the infusion coil 20 out of the guide catheter 30 and to rewind into the coil's original configuration, as shown in FIG. 8. Since the polymer tubing 15 is radiopaque, the infusion coil 20 can be easily observed during deployment on a fluoroscope or other suitable X-ray device.

The deployment catheter includes a first marker 31 at a forward distal end and a second marker 32 spaced axially rearwardly from the first marker 31. The first and second markers 31 and 32 are radiopaque and are spaced apart a distance approximately equal to the axial length of the coil 20 in its relaxed position (FIG. 6). The markers 31 and 32 are used to determine coil placement within a vessel. Because the markers 31 and 32 are radiopaque, they can be observed using a fluoroscope or other suitable X-ray device.

Once the markers 31 and 32 are observed at the desired deployment site, the deployment catheter 26 is twisted and pushed from the guide catheter 30, as described above. The deployment catheter 26 is preferably twisted until the coil portion of the infusion coil 20 assumes an axial length approximately equal to the axial length in its relaxed position.

Figure 9:
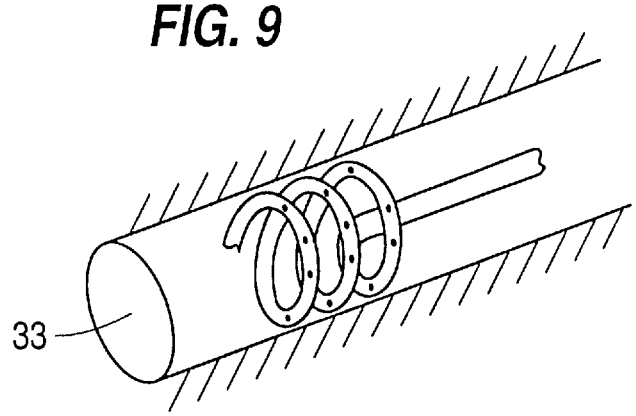
FIG. 9 is a perspective view of the infusion catheter deployed in an artery having a round cross-section.
Figure 10:
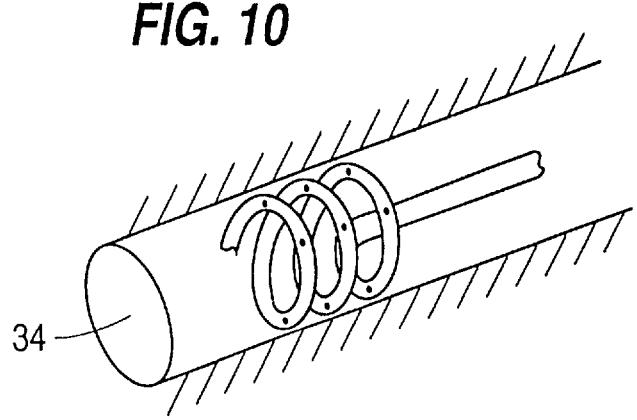
FIG. 10 is a perspective view of the infusion catheter deployed in an artery having an oval or oblong cross-section.

The deployment procedure described above for the second embodiment allows for simple positive deployment of the infusion coil 20. More importantly, the deployment procedure allows for positioning of the device in an irregularly shaped vessel while maintaining a coil configuration that is in contact with the vessel wall along its entire periphery. To illustrate this point, FIG. 9 shows the infusion coil 20 of the second embodiment deployed in an artery 33 having a round cross-section, which is an ideal deployment site for most stents and delivery devices. On the other hand, FIG. 10 shows the infusion coil 20 of the second embodiment deployed in an artery 34 having an oblong or other irregularly shaped cross-section. In both instances, the infusion coil 20 of the present invention is soft enough to conform to any differences and irregularities in the vessel wall. Moreover, the twisting motion ensures that the infusion coil 20 is placed against the vessel wall. A stiffer tube, such as one that relies on polymer resiliency to form a coil, rather than a resilient fiber core as in the present invention, will bridge such irregularities.

Figure 11:
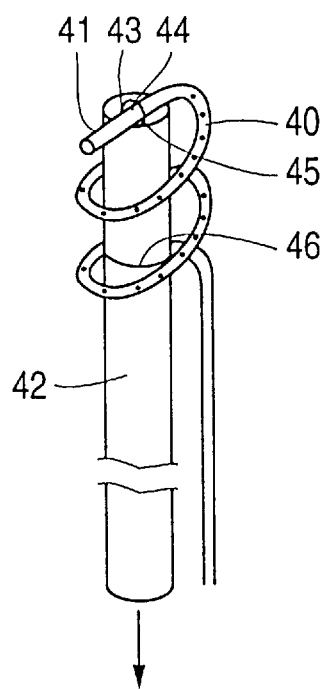
FIG. 11 is a perspective view of an infusion coil, according to a third embodiment of the present invention, in a relaxed position on a deployment catheter.

Referring to FIG. 11, a third embodiment of the present invention will be described. In the third embodiment, an infusion coil 40 with a distal end portion 41 is formed using a resilient fiber core that is preshaped into a forward-feed coil shape, as shown in FIG. 11. A deployment catheter 42 is provided for deploying the infusion coil 40 in a manner similar to that described above for the second embodiment. The deployment catheter 42 includes a notch 43 and a snare device 44 for holding the distal end portion 41 of the infusion coil 40.

With the deployment catheter 42, the distal end of the infusion coil 40 is grabbed in the snare device 44 or similar clamp at the end of the deployment catheter 42. This allows the coil 40 to be dragged into place and twisted, similar to the procedure described above for deploying the infusion coil 20 of the second embodiment. First and second markers 45 and 46 are provided to determine coil placement within a vessel, similar to the markers 31 and 32 of the second embodiment.

Figure 12A:
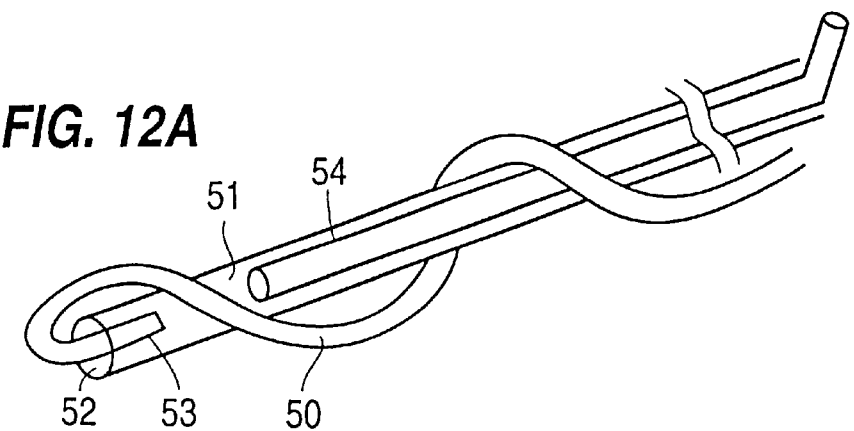
FIG. 12A is a perspective view of an infusion coil held by a friction lock of a deployment catheter according to a fourth embodiment of the present invention.
Figure 12B:
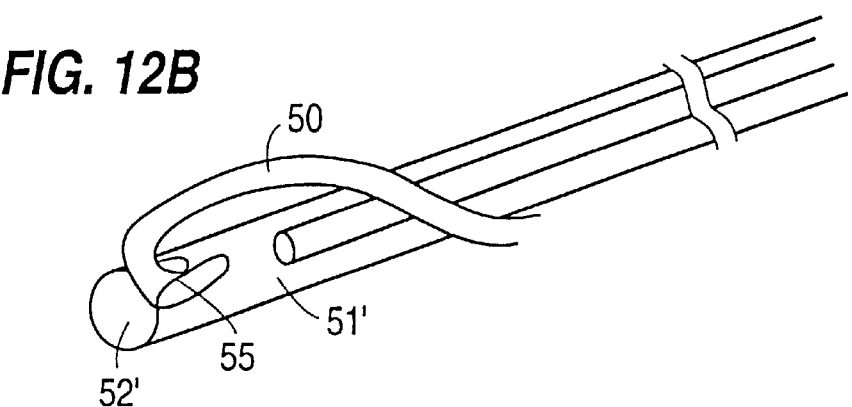
FIG. 12B is a perspective view of the deployment catheter shown in FIG. 12A with a modified friction lock.

FIGS. 12A and 12B illustrate an infusion coil apparatus according to a fourth embodiment of the present invention. As shown in FIG. 12A, the infusion coil apparatus includes an infusion coil 50 having a resilient fiber core that is preshaped into a forward-feed coil shape, as in the first and third embodiments. A deployment catheter 51 is provided for deploying the infusion coil 50 in a manner similar to that described above for the third embodiment.

The deployment catheter 51 includes a friction lock 52 formed in a distal end thereof for receiving and holding a distal end 53 of the infusion coil 50. The friction lock 52 comprises an axially extending bore at the end of the deployment catheter 51 into which the distal end 53 of the infusion coil 50 is inserted. The resilient nature of the infusion coil 50 created by the resilient fiber core creates a friction holding force between the infusion coil 50 and the axially extending bore upon insertion of the distal end 53 of the infusion coil 50 into the axially extending bore.

A push rod 54 is inserted into the deployment catheter 51 to release the friction lock 52 between the infusion coil 50 and the deployment catheter 51 after the infusion coil 50 is positioned in a vessel at a desired location. To release the friction lock 52, the push rod 54 engages and pushes the distal end 53 of the infusion coil 50 out of the axial bore of the deployment catheter 51.

As with the second and third embodiments described above, the deployment catheter 51 of the fourth embodiment, in operation, drags the infusion coil 50 into place and deploys the infusion coil 50 into a desired deployment location. The deployment catheter 51 can also be provided with radiopaque markers (not shown) to facilitate observation on a fluoroscope or other suitable X-ray device.

FIG. 12B is a perspective view of a deployment catheter 51' with a modified friction lock 52'. The modified friction lock includes a notch 55 in a side wall of the distal end of the deployment catheter 51'. In use, the infusion coil 50 is inserted into the axial bore of the deployment catheter 51' and positioned such that a distal end portion of the infusion coil 50 is received in the notch 55. The notch 55 facilitates twisting of the infusion coil 50 during deployment to rewind the infusion coil 50 into its original configuration.

Referring to FIGS. 13A to 13C, an infusion coil and deployment apparatus according to a fifth embodiment of the present invention will be described.

The infusion coil 60 and deployment catheter 61 used in the fifth embodiment are essentially the same as the infusion coil 50 and deployment catheter 51 used in the fourth embodiment. Specifically, the deployment catheter or distal coil holding tube 61 includes a friction lock 62 in the form of an axial bore for securing a distal end 63 of the infusion coil 60 during deployment. A push rod 64 is provided within the distal coil holding tube 61 to release the friction lock 62. In addition, the deployment apparatus includes a proximal holding tube 65 positioned over a linear portion 66 of the infusion coil 60. A containment sheath 67 is disposed over both the proximal and distal holding tubes.

The assembly shown in FIGS. 13A to 13C is particularly useful in instances when a physician desires the ability to position and adjust (compress, elongate, etc.) the infusion coil 60. This is done by first grabbing the distal end 63 of the infusion coil 60 with the friction lock 62, as previously described, and also grabbing the proximal, linear portion 66 of the infusion coil 60 using the proximal holding tube 65. The proximal holding tube 65 is slid over the infusion coil 60 into a position abutting the coiled portion of the infusion coil 60. The proximal holding tube 65 is then clamped or otherwise secured to the infusion coil 60 at the proximal end of the infusion coil 60 outside the containment sheath 67 (at the hub of the deployment apparatus).

In a pre-deployed state of the infusion coil assembly (FIG. 13B), the proximal holding tube 65 and the distal holding tube 61 are slid in opposite directions to elongate the coil 60 and are then pulled into the sheath 67. To deploy the device, the distal holding tube 61 is pushed out of the sheath 67 followed by the proximal holding tube 65 (FIG. 13A). The distal and proximal holding tubes 61, 65 can then be manipulated by the physician to compress and elongate the infusion coil 60 as desired.

Figure 14:
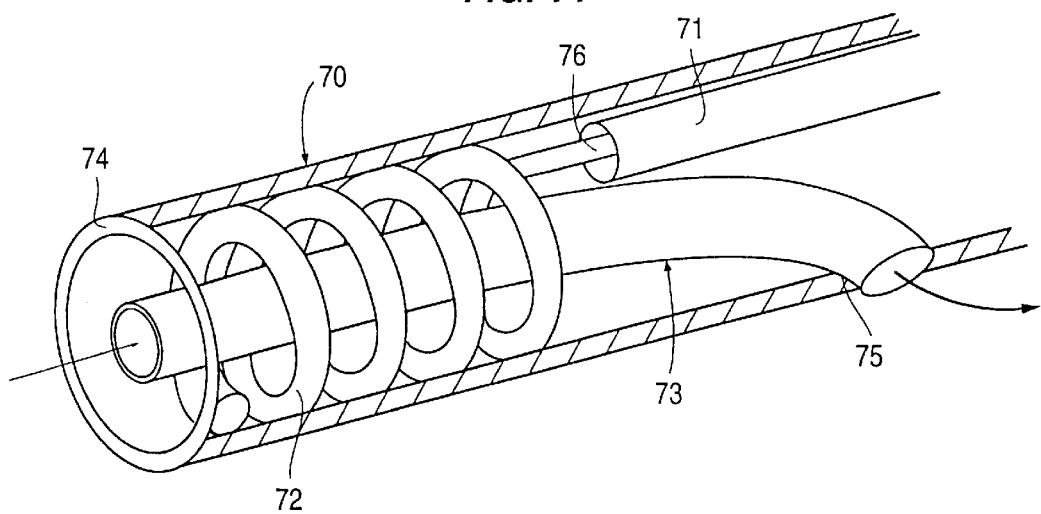
FIG. 14 is a perspective view of a sixth embodiment of the present invention for deploying the infusion coil assembly over a guide wire.

Referring to FIG. 14, a sixth embodiment having a modified deployment assembly for deploying an infusion coil over a guide wire will be described. Guide wires for guiding catheters and deployment devices into a desired location in a vessel of a patient are well known.

As shown in FIG. 14, a modified delivery sheath 70 and push tube 71 are provided for deploying the infusion coil 72 over an existing guide wire (not shown). A guide tube 73 extends from a front opening 74 of the delivery sheath 70 to an opening 75 in a side wall of the delivery sheath 70. The guide tube 73 is permanently secured to the side wall of the delivery sheath 70 by a suitable adhesive or thermal bonding process. The guide tube 73 has an inner diameter large enough to permit the guide wire to pass freely therethrough.

The infusion coil 72 is loaded in the delivery sheath 70 by inserting the linear portion 76 of the infusion coil and push tube 71 into the delivery sheath 70 through the front opening 74. In its loaded position, the coiled portion of the infusion coil 72 is positioned coaxially about the front portion of the guide tube 73. In this manner, the infusion coil 72 can be easily pushed out of the delivery sheath 70 during deployment.

In operation, a proximal end of a guide wire extending outside of a patient is inserted into the front end 77 of the guide tube 73 and pushed through the guide tube 73 until the guide wire exits through the opening 75 in the side wall of the delivery sheath 70. The proximal end of the guide wire is then held by the physician while the loaded delivery sheath 70 and infusion coil assembly are pushed into the vessel of the patient to the desired location using the guide wire for guidance.

The guide tube 73 and modified delivery sheath 70 permit deployment of the infusion coil assembly over an existing guide wire without removing the guide wire and without requiring a guide wire extension to be attached to the guide wire. With the present arrangement, only a short portion of the guide wire must be exposed outside of the patient to permit the delivery sheath 70 to be introduced over the guide wire and into the patient.

By way of example, a 0.016 to 0.018 inch diameter guide wire may be used for a 0.14 inch internal vessel diameter. The guide tube 73 in this example preferably has a 0.020 inch internal diameter (0.022 inch external diameter), and the delivery sheath preferably has a 0.058 inch internal diameter (0.065 inch external diameter).

Figure 15:
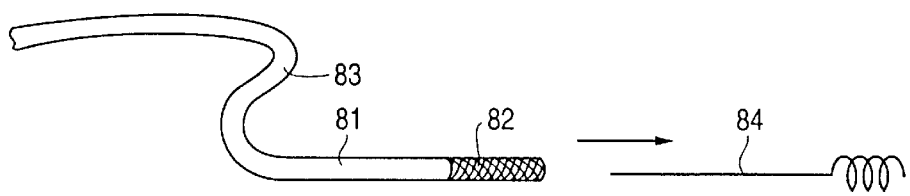
FIG. 15 is an exploded perspective view of an infusion coil showing an alternate construction of the polymer tubing according to the present invention.
Figure 16:
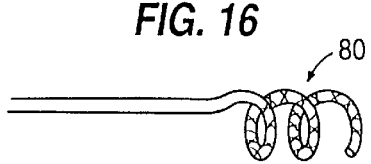
FIG. 16 is an assembled perspective view of the infusion coil shown in FIG. 15.

Referring to. FIGS. 15 and 16, an alternate construction of an infusion coil 80 according to the present invention will be described. This alternate construction can be used for any of the coil shapes of the first three embodiments described above, as well as other similar devices.

The polymer tubing 81 of the coil 80 is formed from a braided, stitched or porous tube, such as nylon braids, PVDF porous tubing, or PTFE porous tubing. For a typical catheter construction, the tubing 81 (preform) is cut to approximately 4' to 5' long. The first 95% of the braid/stitch/porous tubing 81 is consolidated by placing the tubing (preform) on a mandrel and heat consolidating the tubing (preform) with a heat shrink, or coating/impregnating the tubing (preform) with a urethane or similar material.

The result of this process, as shown in FIG. 15, is a polymer tubing 81 with a porous or braided end portion 82 and a consolidated (i.e., non-porous) main portion 83. The polymer tubing 81 is then placed over a resilient fiber core 84, as in the previous embodiments. The final result, as shown in FIG. 16, is a soft infusion coil 80 having a porous polymer coating 82 for delivering fluid-based agents about the circumference of the coil.

The soft polymer tubing 81 of the present invention is preferably constructed of a polymer compounded with a radio opacifier at a loading high enough to make it radiopaque. For example, the polymer can be compounded with approximately 75% by weight tungsten. The soft polymer tubing 81 can also be made radiopaque using a suitable coating containing a radio opacifier applied over the polymer tubing.

The distal end of the infusion coil in each of the disclosed embodiments can be sealed or closed in a number of ways according to the present invention. In some applications, particularly where the coiled portion of the polymer tubing is highly porous, it may be unnecessary to close the distal end of the infusion coil. However, in other applications, particularly where a limited number of openings are provided for delivery of fluid-based agents through the polymer tubing, it may be important to close or seal the distal end to prevent the fluid-based agents from flowing out the end of the infusion coil instead of through the delivery openings.

Figure 17A:
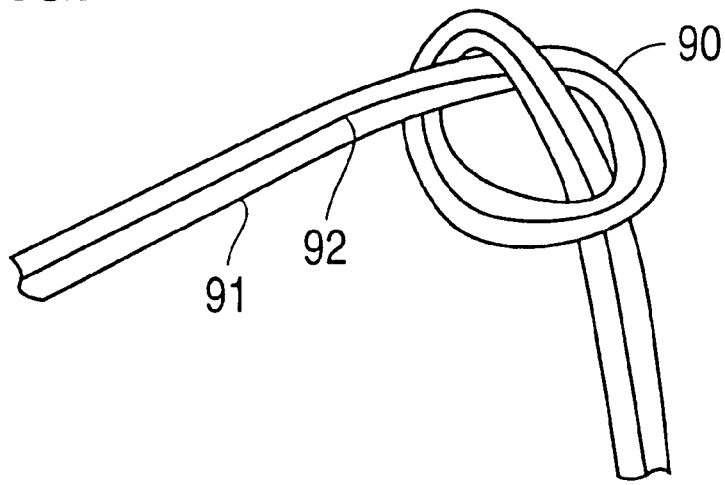
FIGS. 17A to 17C show a series of steps for sealing the distal end of the infusion coil by knotting and thermally consolidating the end of the infusion coil.
Figure 17B:
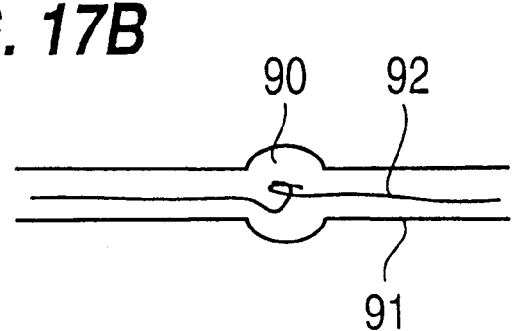
Figure 17C:
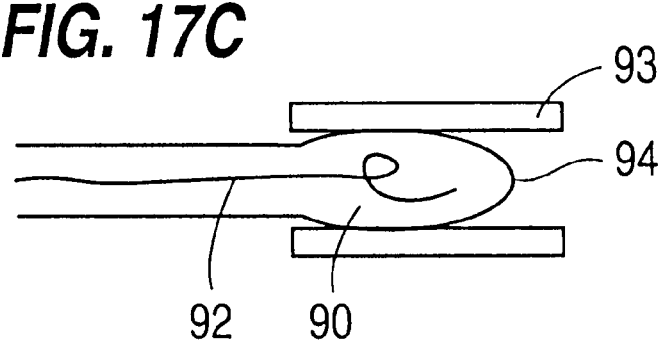

A first way of sealing the distal end of the infusion coil is to knot and consolidate the end of the infusion coil, as shown in FIGS. 17A to 17C. As shown in FIG. 17A, a knot 90 is formed in the end of the infusion coil with both the polymer tubing 91 and the resilient fiber core 92. The knot 90 is then pulled tight, as shown in FIG. 17B, and the excess polymer tubing 91 and resilient fiber core 92 extending past the knot 90 are cut off. The knot 90 is then preferably covered by a short length (e.g., 1–2 mm) of heat shrink tubing 93 (e.g., plastic), as shown in FIG. 17C. The heat shrink tubing 93 is heated and shrunk so that the heat shrink tubing 93 flows over the cut end 94 of the infusion coil and permanently consolidates the knot 90 and heat shrink tubing 93 at the distal end of the infusion coil. As a result, the resilient fiber core 92 is permanently anchored within the polymer tubing 91, and the distal end of the infusion coil is sealed to prevent fluid-based agents from flowing therefrom.

A second way to seal the distal end of the infusion coil is to dip the end of the polymer tubing in a potting agent, such as medical grade silicon, cyanoacrylate, or other suitable adhesive. The potting agent moves into the polymer tubing by capillary action and then cures to form an effective seal and anchor for the resilient fiber core in the end of the infusion coil.

A third way to seal the distal end of the infusion coil is to merely stretch the polymer tubing past the end of the resilient fiber core. Upon stretching a sufficient length, the polymer tubing necks down and permanently sets in such a way as to close the end of the polymer tubing against the flow of fluid-based agents therethrough. The result is a feathered, closed portion of the polymer tubing that extends slightly past the end of the resilient fiber core.

Figure 18:
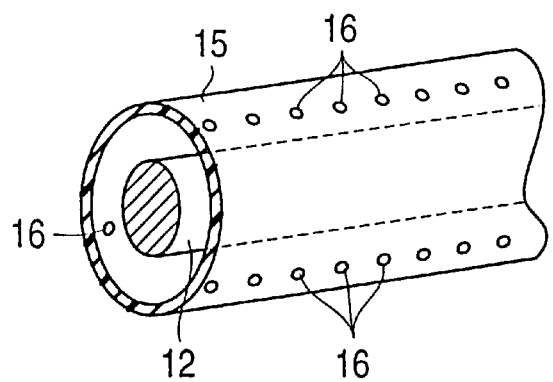
FIG. 18 is an enlarged perspective view of the infusion coil showing a plurality of circumferentially spaced rows of openings for permitting delivery of diagnostic and therapeutic agents through the polymer tubing.

As explained above, holes 16 may be formed in the polymer tubing of the infusion coil by drilling, lasing, machining, punching, and so forth. The holes 16 are preferably formed in the polymer tubing in a plurality of circumferentially spaced rows extending along the length of the coiled portion of the polymer tubing 15. For example, as shown in FIG. 18, three rows of holes 16 can be formed in the polymer tubing 15 with each row of holes 16 being spaced 120 degrees apart from the other rows. The circumferentially spaced rows of holes 16 provide two significant advantages. First, the multiple rows of holes 16 ensure that fluid-based agents will flow about an upstream surface of the coiled portion of the polymer tubing 15 to prevent blood clotting at the point where the blood initially contacts the polymer tubing 15. Second, the multiple rows of holes 16 provide manufacturing convenience in that it is unnecessary to take into account the circumferential location of the holes 16 when forming the coiled portion of the infusion coil.

Figure 19:
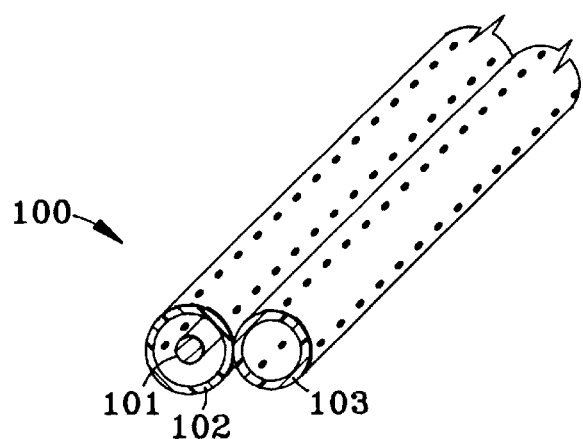
FIG. 19 is a cross-sectional view of a first multiple lumen infusion coil apparatus according to the present invention.
Figure 20:
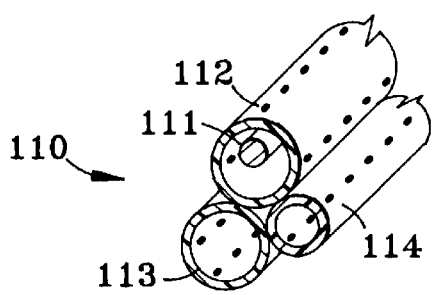
FIG. 20 is a cross-sectional view of a second multiple lumen infusion coil apparatus according to the present invention.
Figure 21:
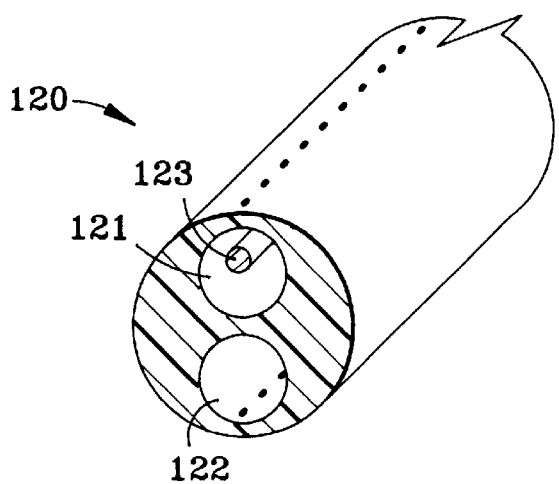
FIG. 21 is a cross-sectional view of a third multiple lumen infusion coil apparatus according to the present invention.

As shown in FIGS. 19 to 21, multiple lumen infusion coils incorporating the features of the present invention can be formed for delivering fluid-based agents and/or withdrawing fluid samples. The particular shape of the multiple lumen infusion coils shown in FIGS. 19 to 21 can be any of the coil shapes described in this application and shown in the other drawings. Similarly, the particular deployment method used for the multiple lumen infusion coils can be any of the methods described herein and shown in the drawings.

The multiple lumen infusion coil 100 shown in FIG. 19 includes a resilient fiber core 101 having a first linear portion and a second portion (not shown) which is preshaped into a coiled shape as in the previously described embodiments. A polymer tubing assembly in this embodiment includes a first polymer tubing 102 secured to a second polymer tubing 103 in a side-by-side manner, each polymer tubing having a lumen extending along a length thereof. The first polymer tubing 102 is slid over the resilient fiber core 101, and the infusion coil 100, including both the first and second polymer tubings 102, 103, takes the shape of the resilient fiber core 101. Thus, a multiple lumen infusion coil 100 is provided, which is capable of separately delivering fluid-based agents through the respective lumens of the first and second polymer tubings 102, 103 and/or withdrawing fluid samples.

As shown in FIG. 20, a multiple lumen infusion coil 110 can also be provided having first, second and third polymer tubings 112, 113, 114 secured together with three distinct lumens for separately delivering fluid-based agents and/or withdrawing fluid samples. As in the embodiment shown in FIG. 19, a single resilient fiber core 111 extends through the lumen of one of the polymer tubings 112, which is sufficient to cause all of the polymer tubings 112, 113, 114 to adapt to the coiled shape of the resilient fiber core As shown in FIG. 21, a multiple lumen infusion coil 120 according to the present invention can also be made by forming multiple lumens 121, 122 through a one-piece polymer member. A resilient fiber core 123 extends through one of the lumens 121 to cause the infusion coil 120 to adapt to a coiled shape of the resilient fiber core 123. In each of the multiple lumen embodiments shown in FIGS. 19 to 21, the polymer tubing must be made from a very soft and flexible polymer material to permit the polymer tubing to adapt to the shape of the resilient fiber core when the infusion coil is deployed.

Figure 22:
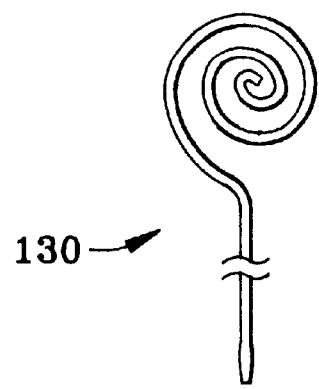
FIG. 22 shows an infusion coil apparatus according to the present invention having a spiral shape in plan view.
Figure 23:
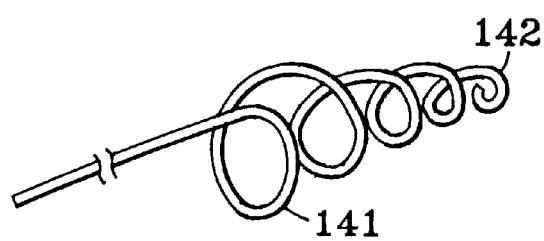
FIG. 23 shows an infusion coil apparatus according to the present invention having a helical shape tapering from a large proximal end to a small distal end.
Figure 24:
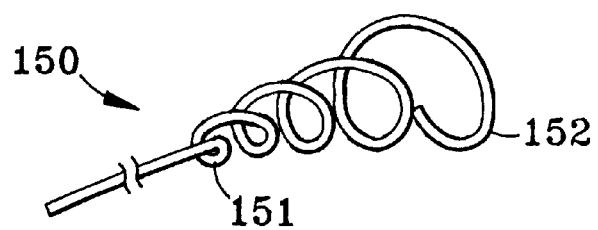
FIG. 24 shows an infusion coil apparatus according to the present invention having a helical shape tapering from a small proximal end to a large distal end.

Referring to FIGS. 22 to 24, additional embodiments of the present invention will be described. Specifically, FIG. 22 shows an infusion coil 130 having a spiral shape in plan view, FIG. 23 shows an infusion coil 140 having a helical shape tapering from a large proximal end 141 to a small distal end 142, and FIG. 24 shows an infusion coil 150 having a helical shape tapering from a small proximal end 151 to a large distal end 152.

In each of the embodiments shown in FIGS. 22 to 24, an infusion coil is formed using a resilient fiber core which is preshaped into the particular shape shown in the drawings. A soft polymer tubing is then slid over the resilient fiber core, as in the embodiments described above, and the infusion coil, including the polymer tubing, takes the shape of the resilient fiber core. As in the other embodiments of the present invention described above, the polymer tubing has a lumen extending over its length and openings, pores, braids, or the like for releasing fluid-based agents delivered through the lumen into a vessel.

The shape of the infusion coil can be selected to adapt the infusion coil to a particular use or position within a patient's vessel. For example, the spiral-shaped infusion coil 130 shown in FIG. 22 may be particularly useful in a relatively wide, flat vessel or body cavity, while the helical-shaped infusion coils 140, 150 shown in FIGS. 23 and 24 may be particularly useful in tapered vessels.

Figure 25:
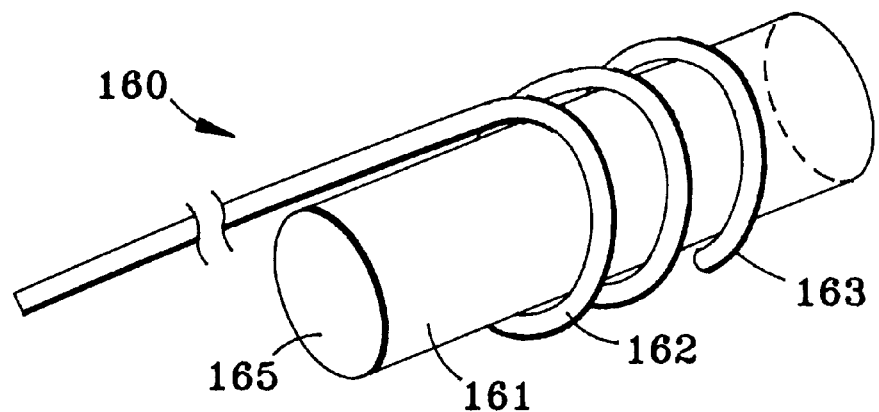
FIG. 25 is a perspective view of an infusion coil apparatus according to the present invention having an inner sheath affixed to a coiled portion of the apparatus.
Figure 26:
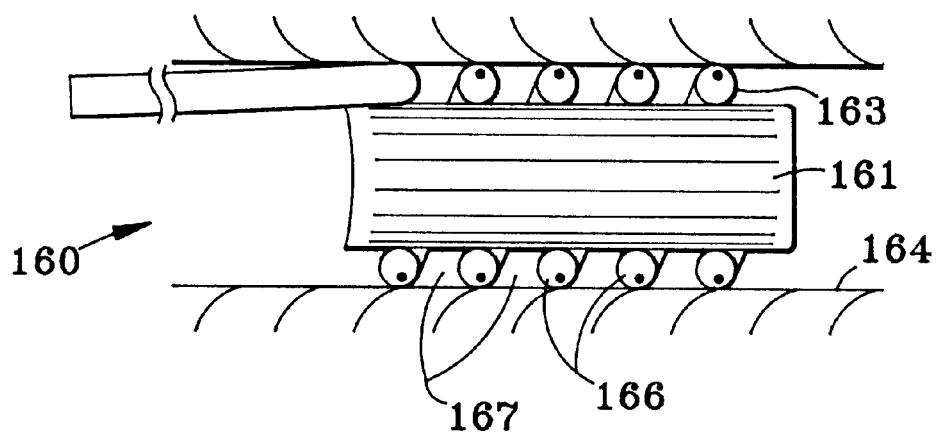
FIG. 26 is a cross-sectional view of the infusion coil apparatus shown in FIG. 25, in a deployed position within a vessel.

Referring to FIGS. 25 and 26, an infusion coil 160 having an inner sheath 161 affixed to a coiled portion 162 of the infusion coil will be described. The infusion coil 160 shown in FIGS. 25 and 26 is essentially the same as the infusion coil 10 shown in FIGS. 1 to 3, except that the inner sheath 161 is affixed to an inner diameter of the coiled portion of the polymer tubing 163.

The inner sheath 161 is preferably a soft flexible tubing that takes the shape of the coiled portion 162 of the infusion coil 160. When the infusion coil 160 is deployed in a vessel 164 (FIG. 26), the inner diameter of the inner sheath 161 defines a passage 165 that permits body fluids to continue flowing through the vessel 164. The outer diameter of the inner sheath 161 and the coils 166 of the infusion coil 160 define pockets 167 along the length of the inner sheath 161. The pockets 167 function to trap fluid-based agents delivered by the infusion coil 160 against the inner wall of the vessel 164 to enhance contact of the agents with the vessel and/or absorption of the agents into the vessel.

Figure 27:
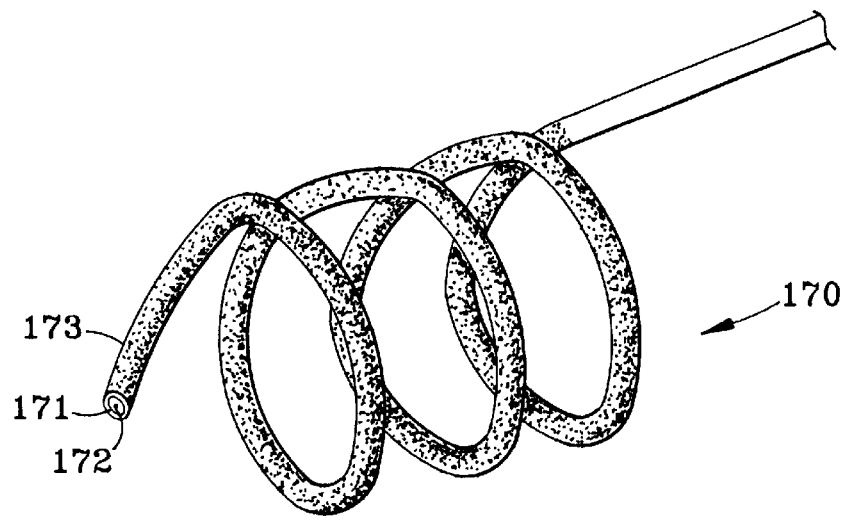
FIG. 27 is a perspective view of a coil apparatus according to another embodiment of the present invention, wherein an outer surface of the polymer tubing is covered with a soluble coating.
Figure 28:
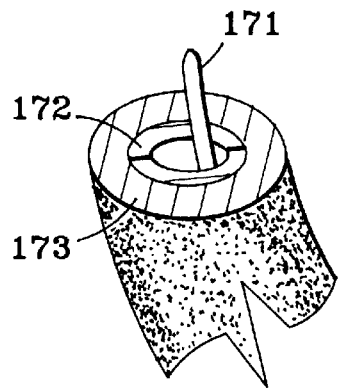
FIG. 28 is an enlarged sectional view of a coated segment of the coil apparatus shown in FIG. 27.

Referring to FIGS. 27 and 28, a coil apparatus 170 having a soluble outer coating will be described. The coil apparatus 170 includes a resilient fiber core 171 that has a first linear portion and a second coil-shaped portion. The particular shape of the coil-shaped portion of the resilient fiber core 171 can be any of the shapes described above. and shown in the accompanying drawings. Similarly, the particular deployment method used for the coil apparatus 170 can be any of the methods described above and shown in the drawings. A forward feed coil shape extending away from the linear portion of the resilient fiber core 171 is shown, for example, in FIG. 27.

A soft polymer tubing 172 is slid or formed over the resilient fiber core 171, and the coil apparatus 170, including the polymer tubing 172, takes the shape of the resilient fiber core 171. An outer surface of the polymer tubing 172 is covered by a soluble coating 173 containing a therapeutic agent. The soluble coating 173 is made of a material that dissolves after the coil apparatus 170 is in place in a blood vessel or the like. Thus, the blood flow or other body fluid dissolves the soluble coating 173 and accomplishes generally the same thing as if a fluid-based drug is infused through the lumen of the polymer tubing 172. The soluble coating 173 can be made, for example, of a gelatin substance in which a therapeutic agent is suspended, or a hollow molecule material that has a therapeutic agent supplanted therein. The soluble coating 173 will leach or break off over time as the substance wets out in a body fluid, such as blood.

The soluble coating 173 placed on the outer surface of the polymer tubing 172 simplifies the introduction of therapeutic agents into the body by making it unnecessary to inject and regulate minute amounts of fluid-based agents through the lumen of the polymer tubing. Moreover, the use of a soluble coating allows a smaller size polymer tubing 172 and resilient fiber core 171 to be used, since no fluid-based agent has to be passed through the lumen of the polymer tubing 172.

For example, the resilient fiber core 171 can be in the form of a spring steel alloy having a diameter of 0.001 to 0.002 inches, and the polymer tubing 172 can have an inside diameter of 0.002 to 0.003 inches and an outside diameter of 0.003 to 0.005 inches. The soluble coating 173 covering the outer surface of the polymer tubing 172 has, for example, a thickness of approximately 0.001 inches, thereby making the overall outside diameter of the coil apparatus 0.005 to 0.007 inches. These dimensions are given by way of example only.

As explained above, the polymer tubing 172 shown in FIGS. 27 and 28 need not have a lumen extending over its length for delivering fluid-based agents through the coil apparatus. Rather, the soluble coating 173 provides the means for delivering therapeutic agents as it dissolves in body fluids.

Figure 29:
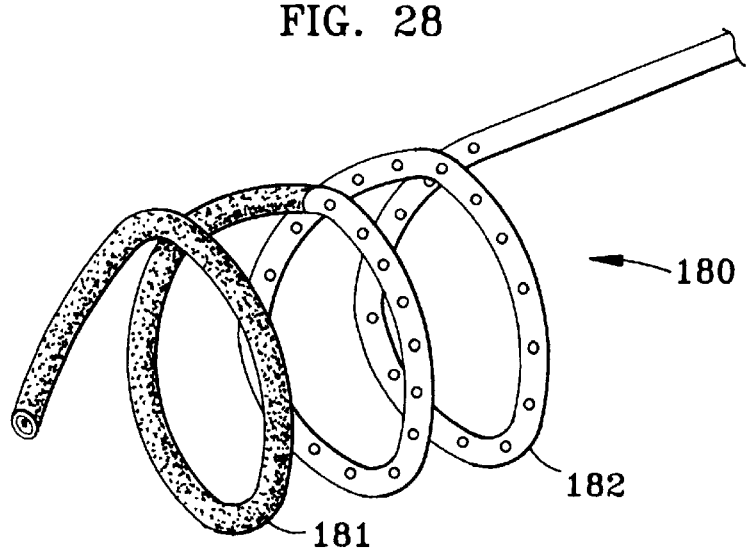
FIG. 29 is a perspective view of a coil apparatus according to another embodiment of the present invention, wherein a first portion of the polymer tubing is covered with a soluble coating, and a second portion of the polymer tubing has openings for delivering fluid-based agents from a lumen thereof.

A coil apparatus 180 according to an alternative arrangement is shown in FIG. 29. The coil apparatus 180 has a soluble coating applied over a first portion 181 of the coiled portion of the polymer tubing, while a second portion 182 of the coiled portion has openings, pores, braids, or the like for releasing fluid-based agents from a lumen of the polymer tubing. This alternative arrangement provides a means for delivering a plurality of therapeutic or diagnostic agents into a vessel, wherein part of the agents are fluid-based and part of the agents are integrated into the soluble coating. This arrangement might be particularly useful, for example, for introducing two or more agents designed to react with each other within the vessel in which the coil is disposed, rather than outside the vessel. A multiple lumen tubing, as described above, could also be used with this arrangement.

Figure 30A:
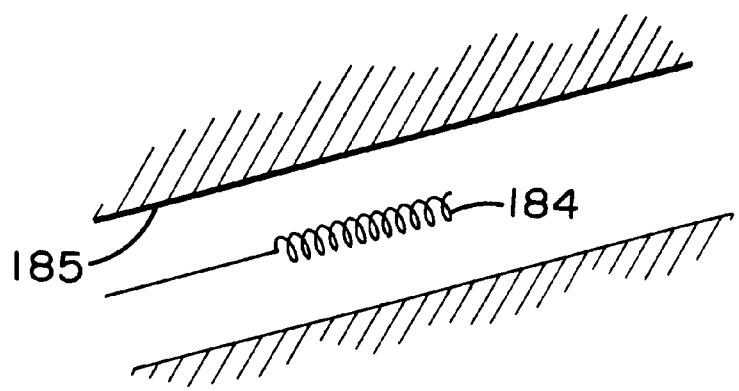
FIGS. 30A, 30B and 30C show a coil deployment method in which a pressure is introduced into a lumen of the coil apparatus to cause the coiled portion to partially unwind and increase in diameter after being placed within a vessel.
Figure 30B:
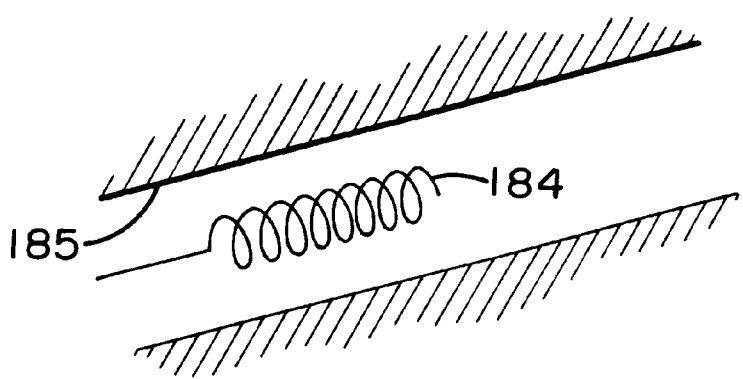
Figure 30C:
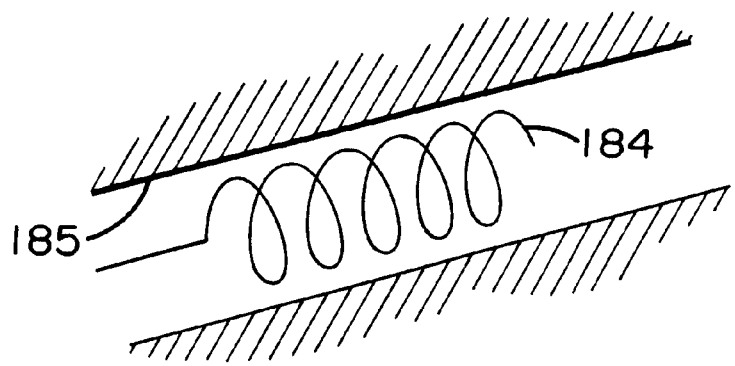

Another method of deploying the coil apparatuses described above is shown in FIGS. 30A, 30B and 30C. This coil deployment method uses a resilient fiber core having a coiled portion that can be much smaller in diameter than the vessel in which the apparatus will be deployed. As described above, the resilient fiber core is covered by a polymer tubing sufficiently soft and flexible to adapt to the shape of the resilient fiber core. This deployment method involves placing the small diameter coiled portion 184 into a vessel 185 and introducing a pressure into the lumen of the polymer tubing covering the coil. The pressure in the lumen is generally uniform throughout the length of the coiled portion 184 and causes the coiled portion 184 to partially unwind and expand in diameter within the vessel 185. FIG. 30A shows the small diameter coiled portion 184 placed in a vessel 185, while FIGS. 30B and 30C show the coiled portion 184 receiving a pressure through its lumen that causes the coiled portion 184 to partially unwind and expand in diameter.

The pressure for unwinding the coiled portion 184 can be present as a result of infusing media through the coil apparatus, or the pressure can be applied for the sole purpose of unwinding the coiled portion 184. In the case where drugs are applied as a coating over the outer surface of the coil apparatus, the pressure could be applied for the sole purpose of unwinding and deploying the coil apparatus. On the other hand, where fluid-based agents are infused through and released from the coil apparatus, the pressure for deployment can be applied as the agents are first infused through the coil apparatus. In some applications, it might be desirable to use a higher pressure to unwind the coiled portion, and a lower pressure to maintain the coil apparatus in its deployed position while fluid-based agents are infused at a desired rate. This pressure deployment method is particularly useful for deploying extra long coils that otherwise tend to become tangled when deployed using the other deployment methods described above.

Figure 31:
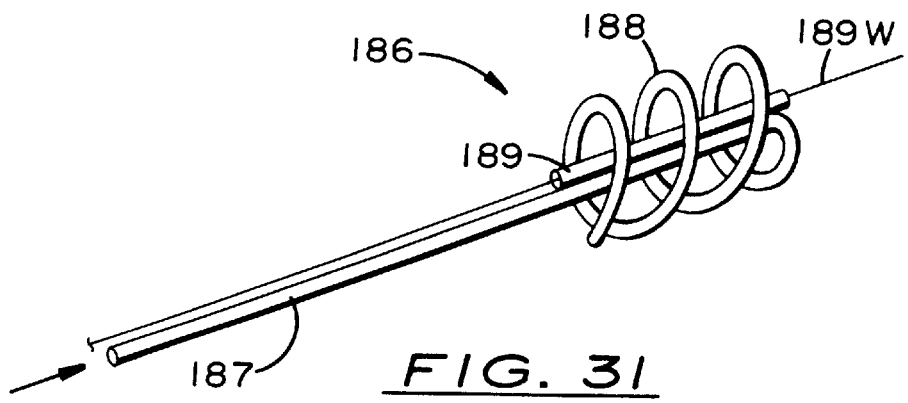
FIGS. 31 and 32 show other coil apparatuses that can be deployed by introducing a pressure into a lumen of the coil apparatus to cause the coiled portion to partially unwind and increase in diameter after being placed within a vessel.
Figure 32:
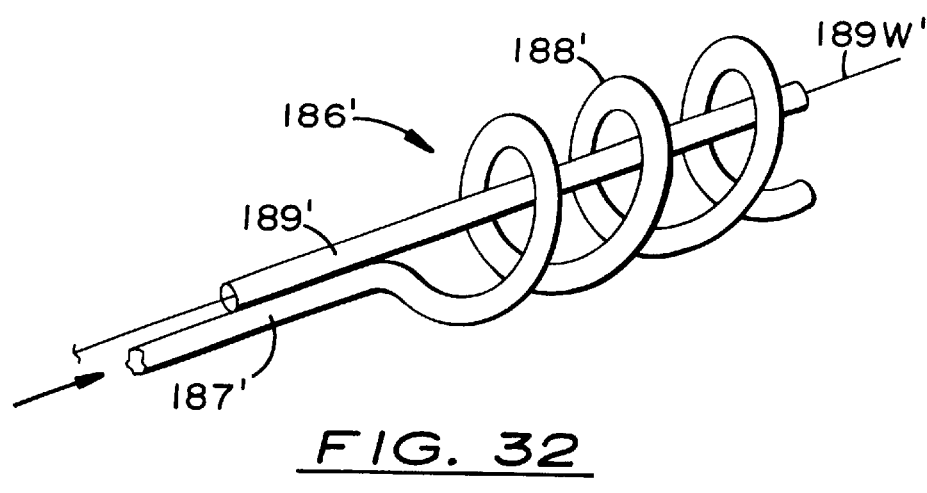

FIGS. 31 and 32 show additional coil apparatuses 186, 186' that are particularly suitable for the pressure deployment method described above. The coil apparatus 186 shown in FIG. 31 has a linear portion 187, a reverse-feed coiled portion 188, and a guide tube 189 placed over a guide wire 189w. The coil apparatus 186' shown in FIG. 32 has a linear portion 187', a forward-feed coiled portion 188', and a guide tube 189' placed over a guide wire 189w'. In each of these embodiments, the coiled portion 188, 188' unwinds and increases in diameter when a pressure is introduced through a lumen of the polymer tubing. For example, the coiled portion 188, 188' in these embodiments can be approximately 2 mm in diameter when the apparatus is first placed in a vessel, and then increased to approximately 3.5 to 6 mm in diameter when pressure is applied through the lumen. The guide tube 189, 189' in each of these embodiments ensures that the coiled portion 188, 188' unwinds and enlarges in a uniform manner.

Another deployment system 210 for deploying the coil apparatuses described above is shown in FIG. 33. This deployment system 210 uses a pair of telescoping, concentric support tubes 211, 212 connected to respective ends 213a, 213b of the coiled portion 213 of the coil apparatus 214. The concentric support tubes 211, 212 can be pushed, pulled and twisted to change the length and diameter of the coiled portion 213 in a precise manner during deployment. For example, to reduce the diameter of the coiled portion 213, the inner support tube 212 can be pushed while the outer support tube 211 is pulled causing the coiled portion 213 to elongate and have smaller diameter coils. Alternatively, the diameter of the coiled portion 213 can be reduced by twisting the outer support tube 211 relative to the inner support tube 212 to cause the coiled portion 213 to be wound tightly around the support tubes 211, 212. The diameter of the coiled portion 213 can be enlarged by reversing the push-pull or twisting techniques.

Figure 33:
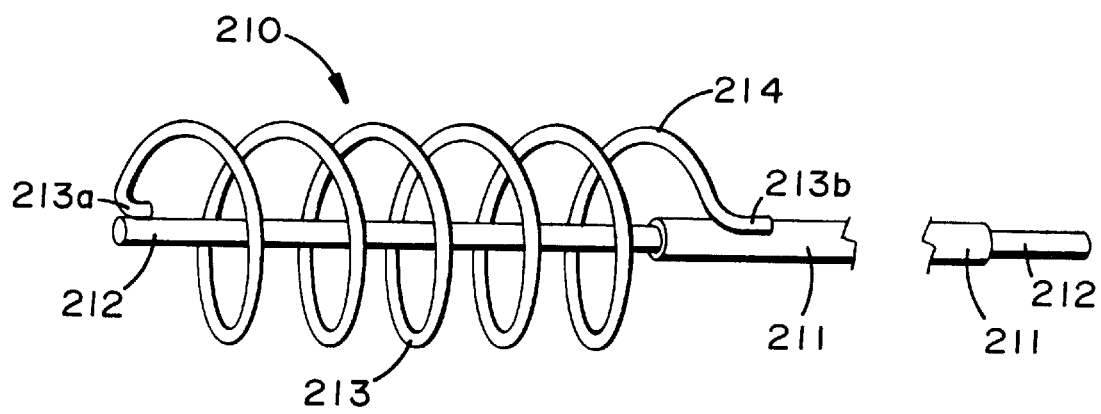
FIG. 33 is a perspective view of a,deployment system using a pair of telescoping, concentric support tubes connected to respective ends of the coil apparatus.

The deployment system 210 shown in FIG. 33 is particularly useful to deploy the coiled portion 213 of the apparatus within a vessel with the coils placed tightly together. For example, if a particular application requires a highly uniform dosage to a short segment of a vessel, the coiled portion 213 can be deployed with its coils placed side-by-side (i.e., in a compacted manner) against the segment of the vessel wall to be treated. This system is especially suitable for long coils that can be deployed in a wide variety of lengths in a vessel.

Figure 34:
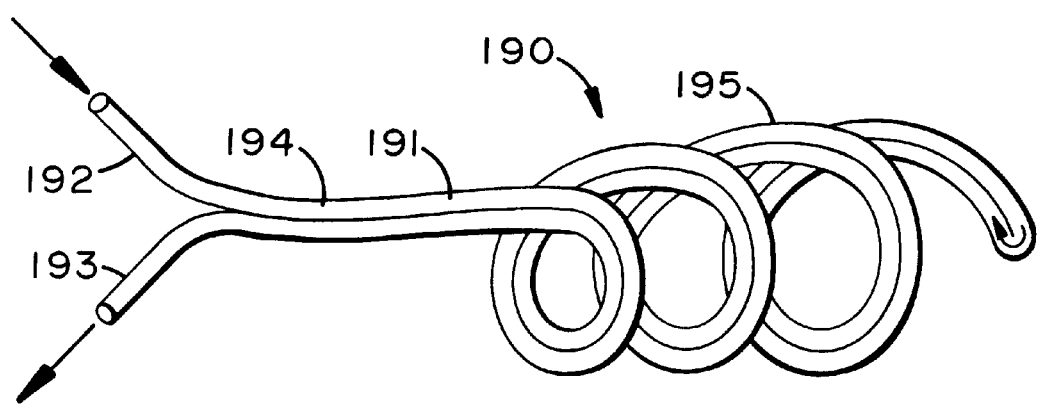
FIG. 34 is a perspective view of a coil apparatus according to another embodiment of the present invention, wherein a polymer tubing having a double lumen is provided for circulating a suspension of radioactive material through the apparatus.

A double lumen coil apparatus 190 according to another embodiment of the present invention is shown in FIG. 34. This coil apparatus 190 includes a polymer tubing 191 having first and second lumens 192, 193 connected together at a distal end of the tubing 191 so that the first lumen 192 provides a supply flow and the second lumen 193 provides a return flow. A resilient fiber core having a linear portion 194 and a coiled portion 195 extends through at least one of the lumens 192, 193 of the polymer tubing 191. As in the other embodiments described above, the polymer tubing 191 encases the resilient fiber core and is sufficiently soft and flexible to adapt to the shape of the resilient fiber core.

The double lumen coil apparatus 190 allows a suspension of radioactive material, such as $^{32}P$ or $^{125}I$ in a liquid carrier, to be circulated through the coiled portion 195 of the polymer tubing and returned through one of the lumens 192, 193. The radiation emitted by such sources is quickly absorbed by surrounding tissue, and will not penetrate substantially beyond the walls of the blood vessel being treated. The radiation dosage can be carefully controlled with this coil apparatus 190 by circulating the radioactive suspension through the coil apparatus 190 for a predetermined time after the coil apparatus is deployed in a vessel. The radioactive suspension can then be emptied from the lumens 192, 193 of the polymer tubing 191 simply by introducing a nonradioactive solution through the polymer tubing 191 before moving the coiled portion 195 from its deployed position in the vessel. The polymer tubing 191 in this embodiment does not have openings or pores for releasing fluid from the lumen since the radioactive material must be carefully monitored and removed from the vessel following treatment. However, an alternative arrangement is contemplated where a third lumen is provided that has openings or pores for releasing a therapeutic agent or the like at the treatment site.

Figure 35:
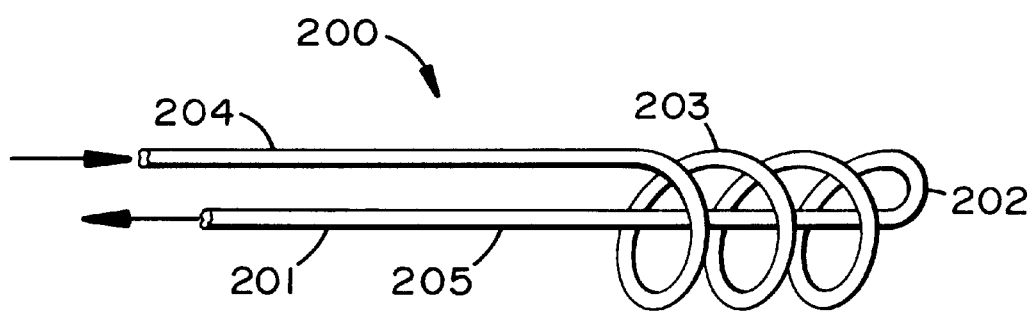
FIG. 35 is a perspective view of a coil apparatus according to yet another embodiment of the present invention, wherein a single lumen polymer tubing is provided for circulating a suspension of radioactive material through the apparatus.
Figure 36:
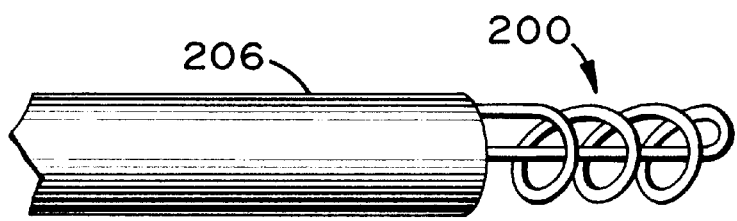
FIG. 36 is a perspective view of the coil apparatus shown in FIG. 35, wherein a deployment sheath having a high density liner is provided to protect a vessel from radiation during deployment of the coil apparatus.

A single lumen coil apparatus 200 according to another embodiment of the present invention is shown in FIGS. 35 and 36. The single lumen coil apparatus 200 includes a resilient fiber core having a linear portion and a coiled portion, and a polymer tubing 201 encasing the resilient fiber core. As in the other embodiments described above, the polymer tubing 201 is sufficiently soft and flexible to adapt to the shape of the resilient fiber core. The polymer tubing 201 continues past a distal end 202 of the coiled portion 203 to provide a return passage for fluid circulated through the coiled portion 203. Thus, the coil apparatus 200 has a supply flow entering the coiled portion 203 through a first linear portion 204 of the polymer tubing 201 and a return flow exiting the coiled portion 203 from a second linear portion 205 of the polymer tubing 201.

The resilient fiber core of the coil apparatus 200 extends through at least the coiled portion 203 and one of the first and second linear portions 204, 205 of the apparatus shown in FIG. 35. Alternatively, the resilient fiber core can be made continuous through both the first and second linear portions 204, 205 and the coiled portion 203 of the polymer tubing 201. In this alternative arrangement, there are no exposed ends of the resilient fiber core that might damage the polymer tubing 201 during use.

A deployment sheath 206 for deploying the coil apparatus 200 in a vessel is shown in FIG. 36. The coil apparatus 200 is introduced into the vessel within the deployment sheath 206, as in the embodiments described above. The deployment sheath 206 is formed of a high density material that absorbs or blocks radiation emitted from the coil apparatus from being delivered to portions of the vessel that are not subject to treatment. For example, once the coil apparatus is deployed in a vessel and a radioactive solution is circulated through the coil apparatus, the deployment sheath 206 will block the radiation emitted from the first and second linear portions 204, 205 of the polymer tubing 201. The deployment sheath 206 can be formed, for example, of a polymer heavily compounded with tungsten or other suitable material for blocking or absorbing radiation. Alternatively, a thin layer of lead tape can be formed over the deployment sheath 206 to block radiation emitted from the apparatus.

The coiled portion of the coil apparatuses 190, 200 shown in FIGS. 34 and 35 can be wound into an extremely tight coil (i.e., a coil having loops that are close together) to provide a more uniform delivery of radiation to the wall of a vessel during treatment. As with the other embodiments described above, the coil apparatuses 190, 200 shown in FIGS. 34 to 36 can be removed from the vessel without difficulty following the radiotherapy treatment.

Figure 37:
FIG. 37 is a perspective view of a coil apparatus having a vent tube inserted through a lumen of the polymer tubing to allow gas and/or fluid to be passed into and out of the coil apparatus.
Figure 38:
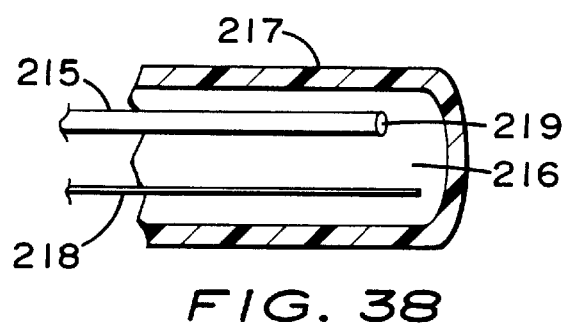
FIG. 38 is a sectional view of an end of the coil apparatus shown in FIG. 37.

As shown in FIGS. 37 and 38, a vent tube 215 can be inserted through a lumen 216 of the polymer tubing 217 beside the resilient fiber core 218 in each of the coil apparatuses described above. The vent tube 215 has an open end 219 at the distal end of the lumen 216 that allows gas and/or fluid to be passed into and out of the distal end of the coil apparatus. Such a vent tube 215 can provide many advantages. For example, the vent tube 215 can be used to bleed air out of the system as the coil apparatus is being filled with fluid, thus making it easier and quicker to. fill. The vent tube 215 can be used to introduce a pressure into the coiled portion for use in the deployment method described above and shown in FIGS. 30A through 30C. The vent tube 215 can also be used as a return passage for a radioactive suspension circulated through the coil, similar to the second lumen in the embodiment described above and shown in FIG. 34.

The vent tube 215 can be made, for example, of polyimide having a 0.004 inch inner diameter and a 0.006 inch outer diameter. This vent tube size would be suitable for placement in a polymer tubing having a 0.014 inch inner diameter and a 0.022 inch outer diameter, along with a wire core having a 0.005 inch diameter. A vent tube of this size would let air pass in and out of the system, but would be too small to pass most fluid suspensions. Thus, a larger vent tube size would be required for circulating a radioactive suspension or the like.

Figure 39:
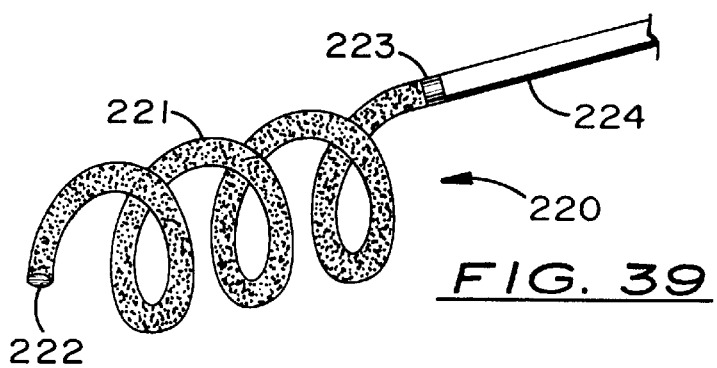
FIG. 39 is a perspective view of a coil apparatus having a coiled portion preloaded with a radioactive material.

The radiotherapy methods described above use a return passage for circulating a radioactive material through a coil apparatus. However, it is also possible to preload a radioactive material into a coil apparatus and to deploy the preloaded apparatus into a vessel. FIG. 39 shows a coil apparatus 220 having a coiled portion 221 preloaded with a radioactive material. A first plug 222 or other suitable means is provided at the distal end of the coiled portion, and a second plug 223 is provided between the coiled portion 221 and the linear portion 224 of the apparatus 220 to keep the radioactive material within the coiled portion 221. The radioactive material used in the preloaded coil apparatus 220 can be in the form of a liquid suspension, a powder, encapsulated balls, or other suitable material capable of holding a radioactive charge. Alternatively, a nonradioactive material, such as metal powder, can be loaded into the lumen of the polymer tubing of the coil apparatus and placed near a source of radiation to acquire a radioactive charge. The nonradioactive material in this case becomes radioactive after it is placed within the tubing, thereby minimizing handling and risk of radiation exposure from the radioactive material. It will be appreciated by those skilled in the art that any of the coil shapes described above can be used for the preloaded apparatus.

Figure 40:
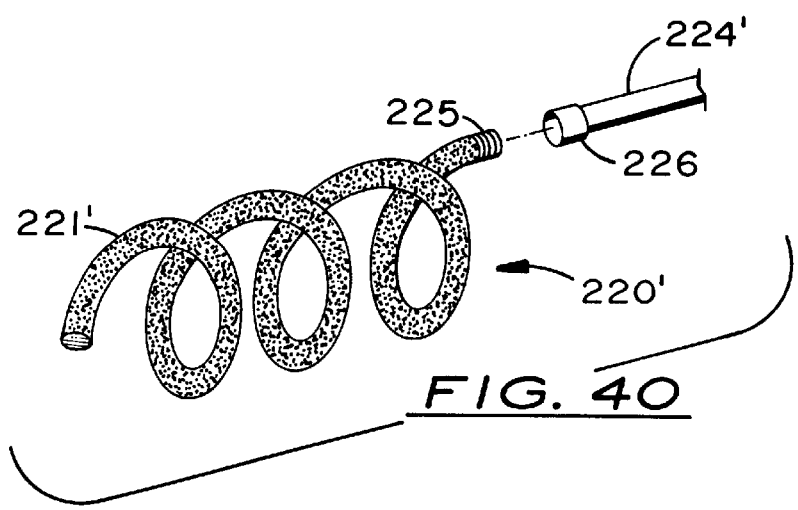
FIG. 40 is a perspective view of a coil apparatus having a coiled portion which is attachable and detachable from a linear portion of the apparatus.

As shown in FIG. 40, a preloaded coil apparatus 220' can have a detachable coiled portion 221' to enable the preloaded (i.e., radioactive) portion of the apparatus to be shipped and stored separately from the rest of the apparatus. A threaded connector having a threaded male end 225 on the coiled portion and a threaded female end 226 on the linear portion 224' is shown in FIG. 40. Other suitable fastening means, such as a friction slip fitting or the like, can be used to attach the coiled portion 221' to the linear portion 224'. A preshaped resilient wire core (not shown in FIG. 40) is used to form the coil shape of this embodiment, as in the other embodiments described above. The linear portion 224' of the apparatus can be formed with or without a resilient wire core depending on the particular material used.

Figure 41:
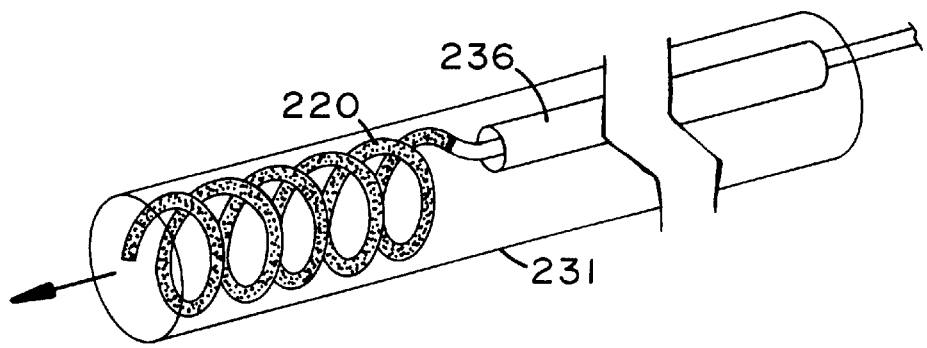
FIG. 41 is a perspective view of the preloaded coil apparatus shown in FIG. 39 placed within a protective deployment sheath.
Figure 42:
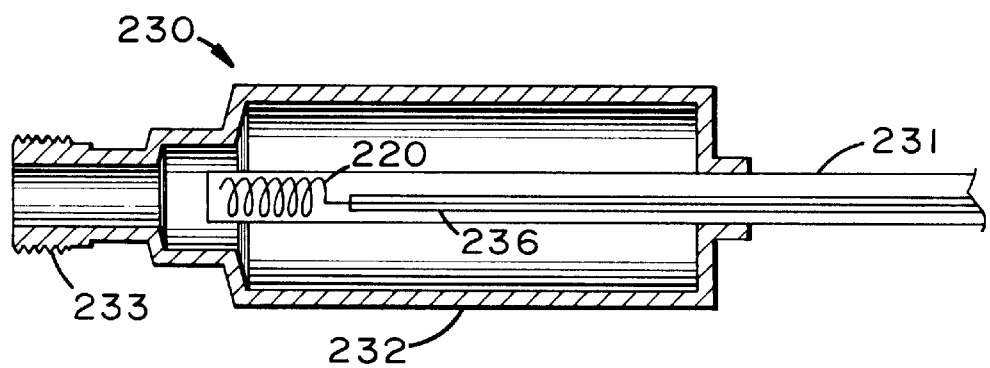
FIGS. 42 and 43 show a deployment system for the preloaded coil apparatus in which the preloaded coil apparatus and deployment sheath are placed in a protective container formed of a high density material to facilitate shipping and handling.
Figure 43:
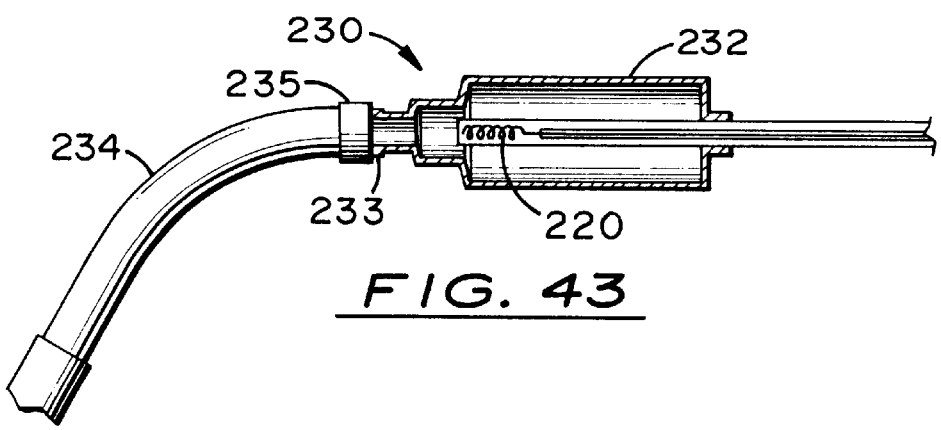

A containment system 230 for handling the preloaded coil apparatus of FIG. 39 is shown in FIGS. 41 to 43. The containment system 230 includes a protective deployment sheath 231, as shown in FIG. 41, in which the preloaded coil apparatus 220 is placed. The preloaded coil apparatus 220 and protective deployment sheath 231 are placed within a protective container 232, as shown in FIG. 42. The protective container 232 is formed of a high density material or with a lead lining to prevent radiation exposure during shipping and handling. The protective container 232 has a Luer lock 233 or other suitable connecting structure for attaching to a guide catheter 234 having a corresponding connecting structure 235. The guide catheter 234 is inserted within a vessel in a known manner.

In operation, the deployment sheath 231 is pushed into the guide catheter 234 until it reaches a desired site in a vessel for treatment. The coil apparatus 220 is then pushed out of the deployment sheath 231 using a push tube 236 for deployment in the manner described above. When the radiotherapy treatment is completed, the coil apparatus 220 is pulled back into the deployment sheath 231 and the protective container 232. The protective container 232 and coil apparatus 220 can then be returned to a supplier for proper disposal or taken to an on-site disposal. The user is thus completely protected from exposure to radiation while handling the preloaded coil apparatus 220.

With the preloaded coil apparatus described above, it is not necessary to infuse or circulate a fluid through the lumen of the tubing. Thus, the amount of radioactive material to be handled and disposed is quite small. Moreover, the apparatus does not need to be against the vessel wall during radiotherapy treatment. Therefore, apparatuses having shapes other than a coil shape can be used for placing the radioactive material in a vessel. Examples of such alternative shapes are described below with reference to FIGS. 44A through 47B of the drawings.

FIGS. 44A through 44D illustrate an apparatus 240 having a flap portion 241 preloaded with a radioactive material for use in radiation treatments. The apparatus 240 has a resilient fiber core 242 preformed into the shape shown in FIG. 44A. The core 242 has a first linear portion 243, a first circular portion 244, a second linear portion 245, a second circular portion 246, and a third linear portion 247. The first circular portion 244 extends between the first and second linear portions, 243, 245, and the second circular portion 246 extends between the second and third linear portions 245, 247. The core 242 is preferably preformed from a continuous member, such as a metal wire or the like.

As shown in FIG. 44B, a nylon or polyimide tubing 248 is placed over the first and third linear portions 243, 247 of the preformed core 242, and a polymer material 249 having a bag shape is placed over the second linear portion 245 and the two circular portions 244, 246 of the preformed core 242 to define a generally cylindrical-shaped flap portion 241. An open end of the polymer material 249 is attached by glue or heat seal to the tubing 248. A closed space is defined by the polymer material 249 for containing a radioactive material 250, as shown in FIG. 44D.

The cylindrical-shaped flap portion 241 shown in FIG. 44B can be rolled around the tubing 248 and placed into a deployment sheath 251, as shown in FIG. 44C. The apparatus 240 is then deployed by placing the deployment sheath 251 into a vessel and pushing the rolled-up apparatus 240 out of the deployment sheath. The flap portion 241 of the apparatus 240 springs into its cylindrical shape upon being pushed out of the deployment sheath 251, thereby providing a uniform dosage of radiation to the vessel while allowing fluid to continue flowing through the vessel.

The tubing 248 is preferably constructed with enough rigidity to roll the flap portion 241 by twisting a proximal end of the tubing 248. For example, a nylon or polyimide tubing having a 0.016 inch inner diameter and a 0.022 inch outer diameter can be used. The deployment sheath 251 is preferably made of a high density material or with a lead liner to prevent radiation exposure before the apparatus 240 is deployed.

An advantage of the apparatus 240 shown in FIGS. 44A through 44D is that a dosage of radiation applied to a treated area of a vessel is more uniform. The core wire 242 in the flap portion 241 of this apparatus 240 has only a negligible shadowing effect on the radiation emitted from the radioactive material 250. In contrast, the shadowing effect caused by the core wire in the coil apparatuses described above is not negligible and must be taken into account by the user. The cylindrical outer surface of the flap portion 241 in its deployed condition also increases the uniformity of the radiation dosage over that provided by a coil-shaped apparatus. The cylindrical-shaped flap portion 241 is flexible enough that the apparatus 240 can be removed from a patient by simply pulling the flap portion 241 back into the deployment sheath 251 when the radiotherapy is completed.

FIGS. 45A through 44C illustrate an apparatus 255 having a plurality of flap portions 256, 257, 258 preloaded with a radioactive material for use in radiation treatments. The apparatus 255 has a resilient fiber core 259 preformed into the shape shown in FIG. 45A. The core 259 is formed by a continuous member and has six circular portions 260 joined at each end by respective linear segments 261. The circular portions 260 of the core are covered by three bag-shaped polymer members 262, 263, 264 to form, respectively, first, second and third flap portions 256, 257, 258. A nylon or polyimide tubing 265 is placed over the linear portions of the core for acting as a support for the flap portions 255, 256, 257. The bag-shaped polymer members 262, 263, 264 are attached to the tubing 265 by glue or a heat seal.

As shown in FIG. 45C, the flap portions 256, 257, 258 are filled with a radioactive material 266, similar to the flap portion 241 shown in FIG. 44D. The apparatus 255 shown in FIG. 45B is deployed and removed in a manner similar to the apparatus shown in FIG. 44B. That is, the flap portions 256, 257, 258 are rolled around the tubing 265 and placed within a deployment sheath formed of a high density material or having a lead liner. During deployment, the flap portions 256, 257, 258 are pushed out of the deployment sheath and caused to spring into the shape shown in FIG. 45B. The apparatus 255 is removed by pulling the flap portions 256, 257, 258 back into the deployment sheath. The space between adjacent flap portions is shown exaggerated in FIGS. 45A and 45B for the sake of clarity. It will be appreciated by those skilled in the art that adjacent flap portions can be placed close together to improve the uniformity of radiation dosage to the treated area.

Figure 46B:
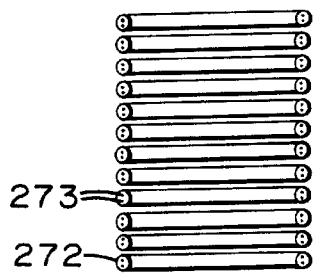
Figure 46A:
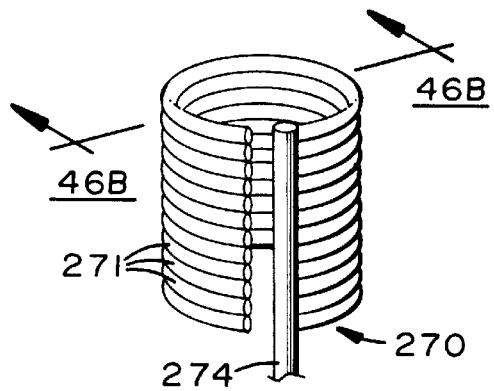

An apparatus 270 having multiple ring portions 271 preloaded with a radioactive material is shown in FIGS. 46A and 46B. The multiple ring portions 271 in this embodiment are formed by placing segments of polymer tubing 272 over a continuous wire core 273. The wire core 273 is preformed into a shape similar to that shown in FIG. 45A, except that many more circular portions are provided. The polymer tubing segments 272 are attached to a nylon or polyimide tubing 274 using glue or a heat seat, as in the embodiments shown in FIGS. 44B and 45B. The polymer tubing segments 272 defining the multiple ring portions 271 are filled with a radioactive material and are sealed by a plug or other suitable means at their free ends.

FIG. 46B shows a sectional view of the ring portions 271 of FIG. 46A. As seen in FIG. 46B, the core wire 273 makes two passes though each segment of polymer tubing 272 to define the shape of the apparatus using a single, continuous core wire 273.

Figure 47B:
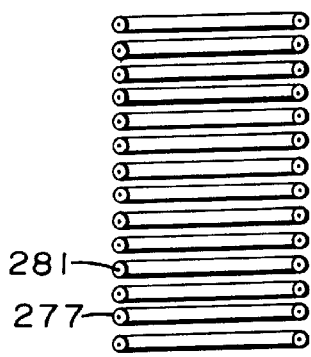
Figure 47A:
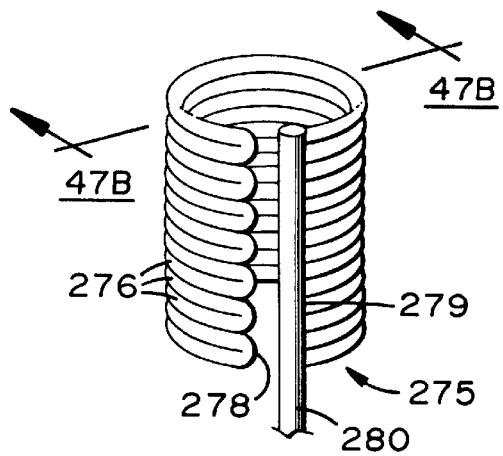

Another apparatus 275 having multiple ring portions 276 is shown in FIGS. 47A and 47B. In this apparatus, each segment of polymer tubing 277 is continuous over two of the ring portions 276. The segments of polymer tubing 277 are folded over at their mid portions 278 and have their ends 279 attached to the support tubing 280 by glue, heat seal, or the like. The core wire 281 is continuous throughout the apparatus and makes only one pass through each of the polymer tubing segments 277, as shown in FIG. 47B. The polymer tubing segments 277 are filled with a radioactive material for use in radiotherapy.

Figure 48A:
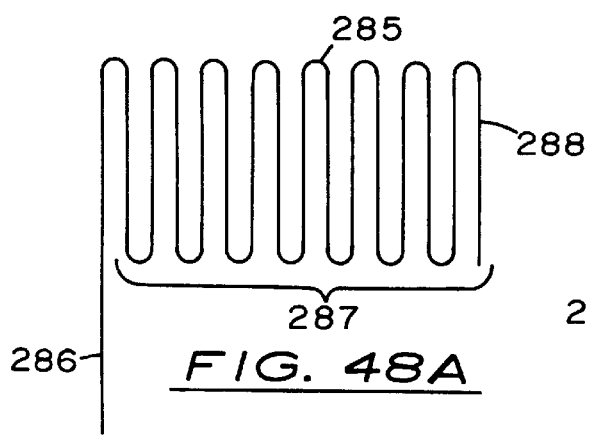
Figure 48B:
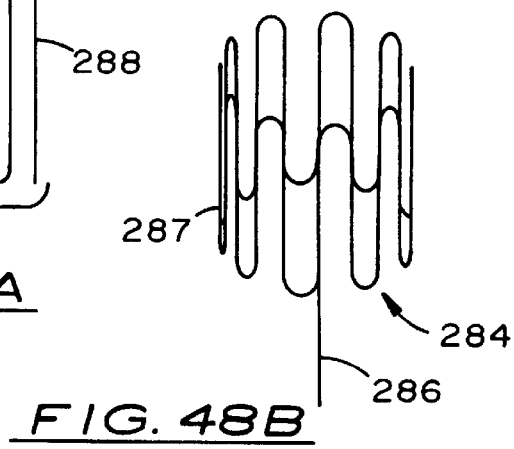

FIGS. 48A and 48B illustrate another apparatus 284 preloaded with a radioactive material. This apparatus 284 has a preformed core wire 285 having a linear portion 286 and a folded end portion 287. The folded end portion 287 has a plurality of folded segments extending generally parallel to the linear portion 286 of the apparatus. The folded segments are formed into a generally cylindrical shape by bending the end portion 287 around and attaching the last folded segment 288 to the linear portion 286. A polymer tubing is placed over the preformed core wire as in the other embodiments described above. The polymer tubing can be preloaded with a radioactive material as described above.

This apparatus 284 can be deployed using one of the deployment methods described above. The folded segments allow the end portion to be compressed into a deployment sheath, and to be deployed by pushing the apparatus out of the deployment sheath so that it springs into an enlarged configuration within a vessel. The shape of this apparatus 284 can also be used in an apparatus to deliver drugs by infusion or with a soluble coating covering the folded segments.

Figure 49:
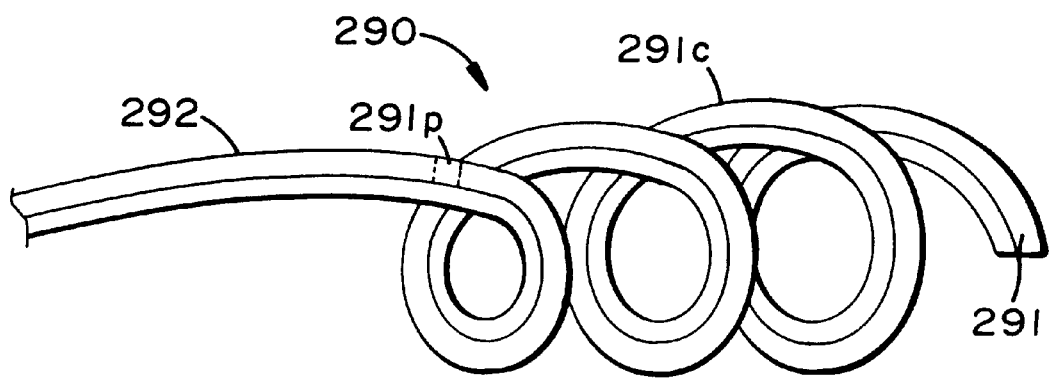
FIGS. 49 and 50 show a perspective and sectional view of a coil apparatus having two lumens with one lumen containing a radioactive material and the other lumen containing a resilient fiber core and providing a passage for introducing a pressure to deploy the apparatus.
Figure 50:
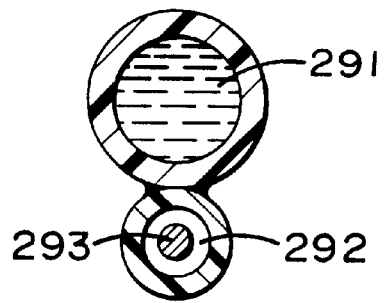

FIGS. 49 and 50 show another coil apparatus 290 for use in radiotherapy. This apparatus has a first lumen 291 containing a plug 291 p and a coiled portion 291 c preloaded with a radioactive material. The apparatus has a second lumen 292 containing a resilient fiber core 293. The second lumen 292 also provides a passage for introducing a pressure to deploy the apparatus 290 in the manner described above with reference to FIGS. 30A through 30C. This apparatus minimizes shadowing (i.e., blocking of the radiation) caused by the resilient fiber core 293 by placing the resilient fiber core 293 in a separate lumen 292 from the lumen 291 containing the radioactive material. Thus, a more uniform application of radiation to a treated area is provided by this coil apparatus 290 as compared to other coil apparatuses described above.

The preloaded apparatuses described above and shown in FIGS. 39, 44B, 45B, 46A, 47A, and 47B, respectively, can be provided with a vent tube, as described above and shown in FIGS. 37 and 38. The vent tube can be used in these configurations to facilitate preloading a radioactive suspension or other fluid into the apparatus, or to circulate a fluid through the apparatus.

As a further improvement to the apparatuses described above, the Applicants have developed various filtration structures for filtering fluids intravascularly. These various filtration structures will be described below with reference to FIGS. 51 to 81 of the accompanying drawings.

Figure 51:
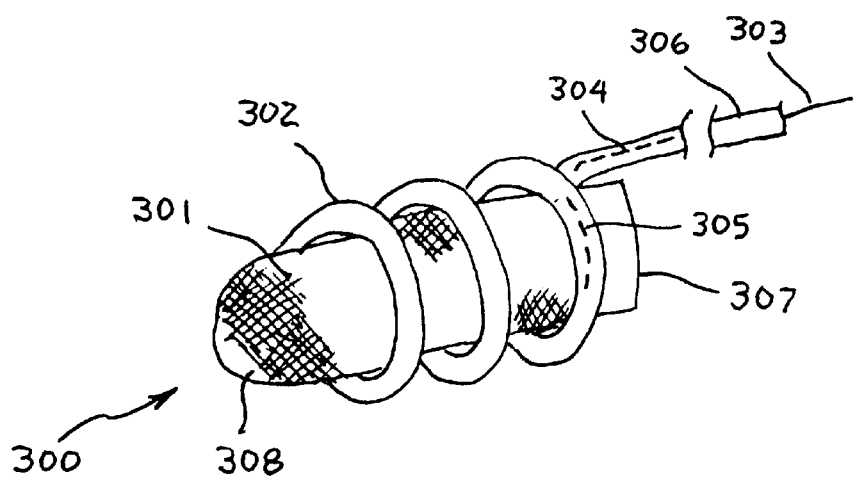
FIGS. 51 and 52 show perspective and sectional views of a coil apparatus having a filtration sock attached to an inner periphery of the coil for filtering intravascular fluids.
Figure 52:
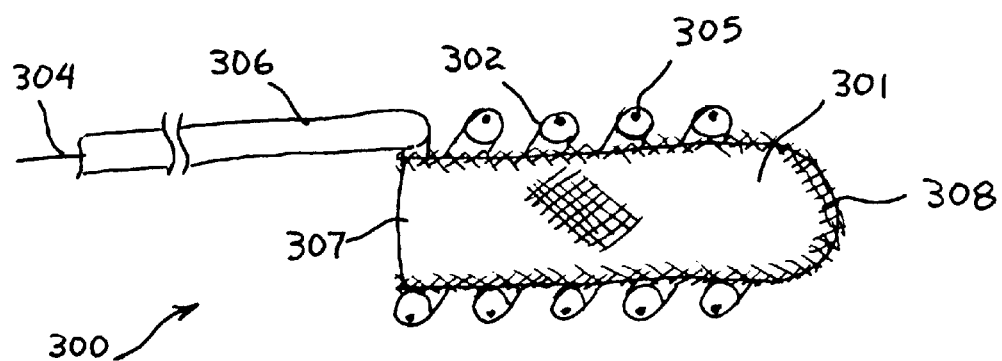

FIGS. 51 and 52 show a coil apparatus 300 provided with a filtration sock 301 attached to an inner periphery of the coiled portion 302. The coil apparatus 300 is similar, for example, to the coil apparatus 10 shown in FIG. I of the drawings and described above. The coil apparatus 300 has a preshaped resilient fiber core 303 having a first linear portion 304 and a second coiled portion 305. The resilient fiber core 303 is encased by a soft, polymer tubing 306 that adapts to the shape of the resilient fiber core 303. The filtration sock 301 is attached to the polymer tubing 306 of the coiled portion 302 by a suitable fastening means, such as glue, thermal welding, stitching, or the like. The filtration sock 301 has an open upstream end 307 for receiving fluids flowing through a vessel, and a closed downstream end 308 for separating particulate from the fluid. The filtration sock 301 is preferably made out of a porous material, such as a weave, braid, or the like. An elastomeric material can also be used for the filtration sock 301 to allow the filtration sock 301 to stretch as necessary for deployment and removal.

Figure 53:
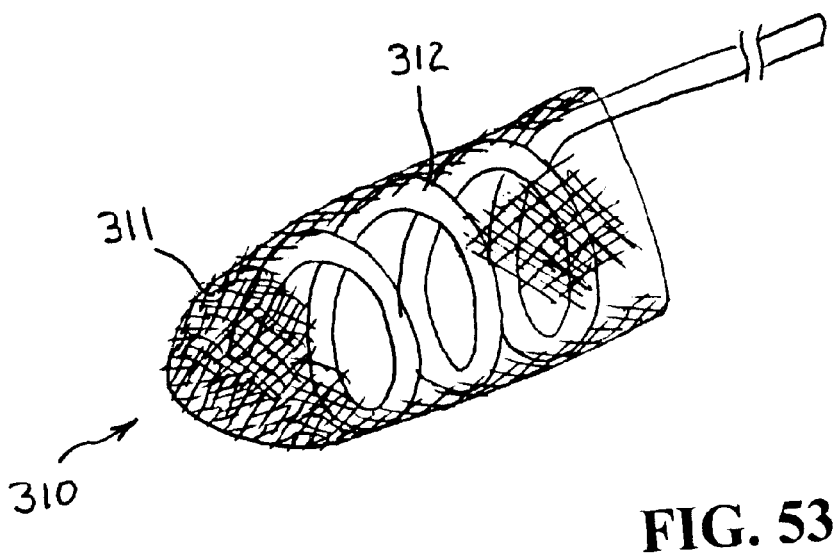
FIGS. 53 and 54 show perspective and sectional views of a coil apparatus having a filtration sock attached to an outer periphery of the coil for filtering intravascular fluids.
Figure 54:
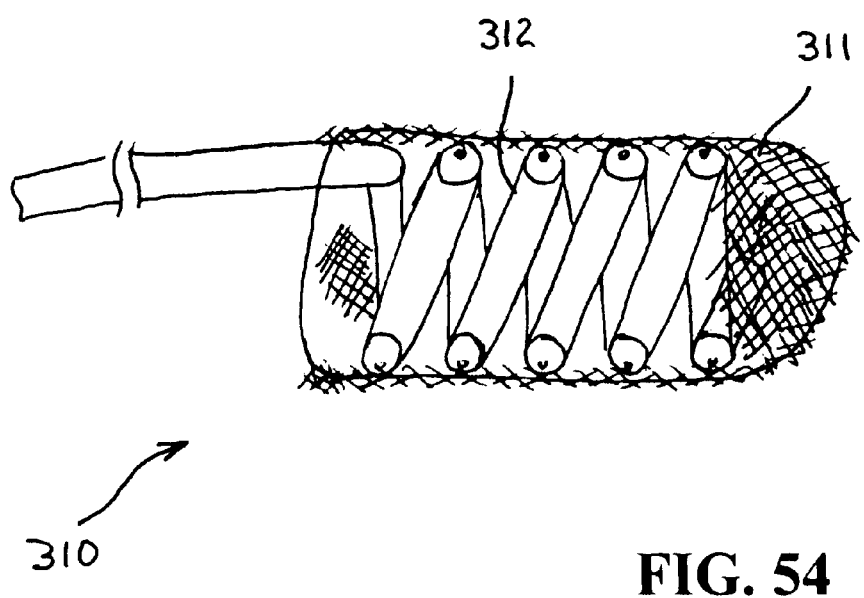

FIGS. 53 and 54 show another coil apparatus 310 having a filtration sock 311 attached to an outer periphery of the coiled portion 312. The coil apparatus 310 is similar to the coil apparatus 300 of FIGS. 51 and 52, except that the filtration sock 311 is attached to the outer periphery of the coiled portion 312 instead of the inner periphery. This allows therapeutic agents to be infused upstream of the closed end of the filtration sock 311, as explained below.

Figure 55:
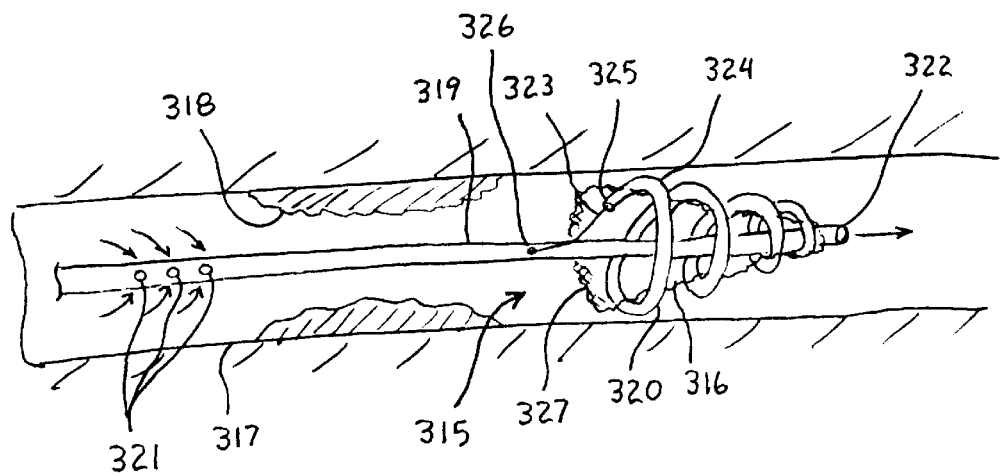
FIGS. 55 and 56 show perspective and sectional views of a helical-shaped coil apparatus with a filtration sock deployed within a vessel and having a central passage that allows noncontaminated fluid to pass downstream of the filtration sock.
Figure 56:
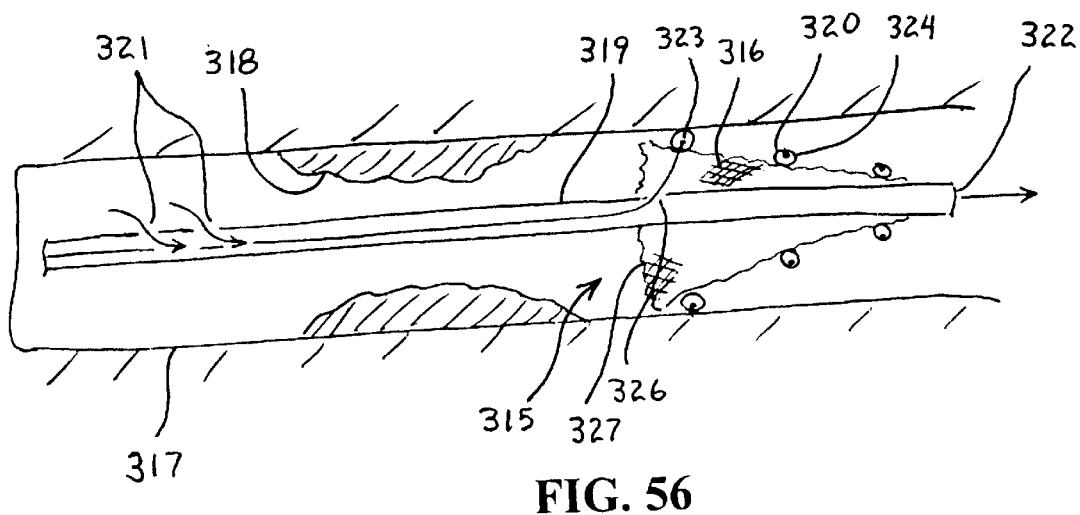

FIGS. 55 and 56 show a conical-shaped coil apparatus 315 with a filtration sock 316 deployed within a vessel 317. The conical shape of the coil apparatus 315 provides an increased flow and filtering area compared to the coil apparatuses 300, 310 shown in FIGS. 51 to 54. As shown in FIGS. 55 and 56, the vessel 317 has an injury area 318, and the coil apparatus 315 is deployed with the filtration sock 316 downstream of the injury area 318. A profusion bypass of the filtration sock 316 is provided by a central tube 319 that extends through a center of the conical-shaped coil 320. The central tube 319 has an upstream portion provided with a plurality of openings 321 into which fluid upstream of the injury area 318 can pass. The noncontaminated fluid passing into the openings 321 flows through the central tube 319 and exits from an open end 322 of the central tube 319 on a downstream side of the filtration sock 316.

The conical-shaped coil 320 is attached to the distal end of the central tube 319 by a suitable fastening means, such as glue or thermal welding. A resilient fiber core 323 is contained within a soft polymer tubing 324 of the conical-shaped coil 320. The resilient fiber core 323 extends from a distal free end 325 of the polymer tubing 324 and passes into the central tube 319 through a small opening 326 in the sidewall of the tube 319. The resilient fiber core 323 can be retracted by an operator to close the large end of the coil 320, and hence, the open end 327 of the filtration sock 316 before the apparatus 315 is pulled into a sheath for removal from the vessel 317. In the deployed position shown in FIGS. 55 and 56, the filtration sock 316 operates to filter particulate, such as blood clots, tissue, and the like, from the fluid flowing downstream of the injury area 318.

Figure 57:
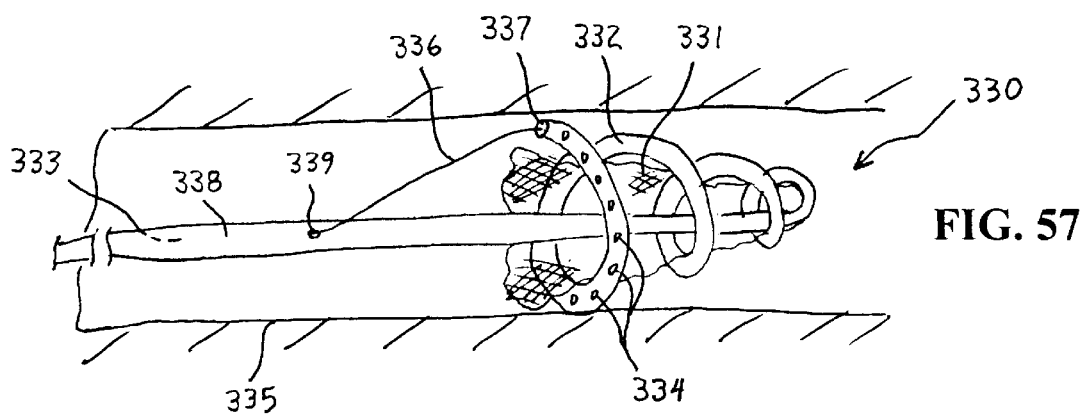
FIGS. 57 and 58 show perspective and sectional views of a helical-shaped coil apparatus with a filtration sock deployed within a vessel and having a central lumen and pores for delivering therapeutic agents over the downstream side of the filtration sock.
Figure 58:
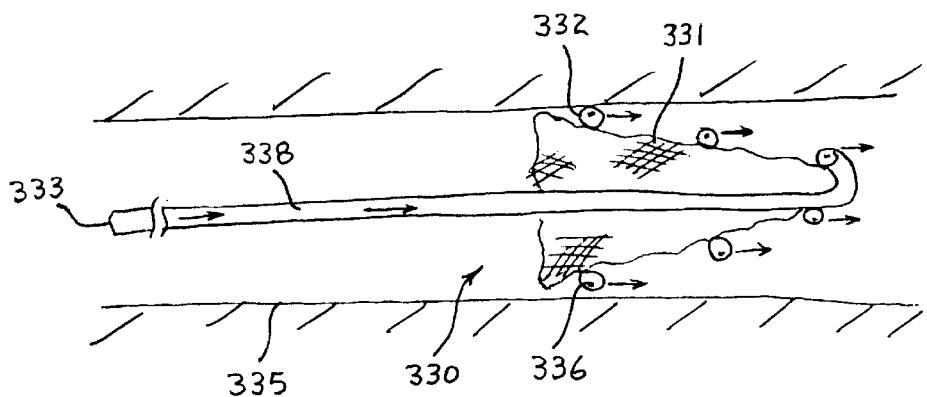

FIGS. 57 and 58 show another conical-shaped coil apparatus 330 with a filtration sock 331 secured to an inner periphery of the coiled portion 332. This coil apparatus 330 has a central lumen 333 and a plurality of pores 334 in the coiled portion 332 for allowing therapeutic fluid to pass from the central lumen 333 through the pores 334 and into the vessel 335. As in the embodiments described above, the pores 334 in the coiled portion 332 can be formed by drilling, lasing, and so forth, or the coiled portion 332 of the tubing can be formed of porous materials, braided, stitched, and so forth to provide suitable porosity for infusing the therapeutic fluids. With the filtration sock 331 secured to the inner periphery of the coiled portion 332, as shown in FIGS. 57 and 58, the therapeutic fluids will be infused primarily downstream of the filtration sock 331. As in the coil apparatus 315 shown in FIGS. 55 and 56, a resilient fiber core 336 extends from a distal free end 337 of the coiled portion 332 of the polymer tubing and passes into the linear portion 338 of the polymer tubing through a small opening 339 in the sidewall of the tubing. The resilient fiber core 336 can be retracted by an operator to close the coil and filtration sock 331 before the apparatus 330 is pulled into a sheath for removal from the vessel 335.

Figure 59:
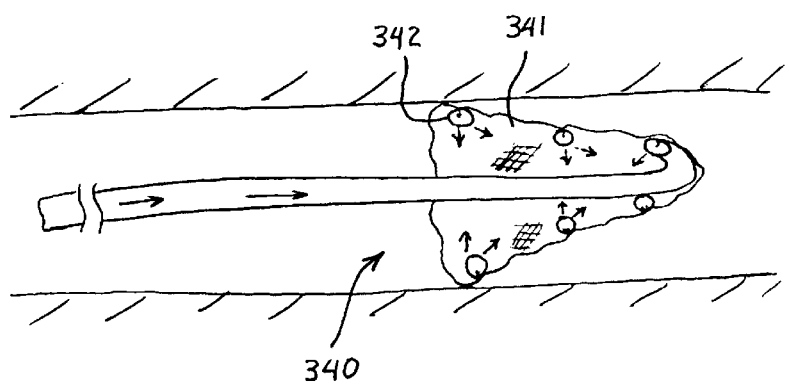
FIG. 59 is a sectional view of a helical-shaped coil apparatus with a filtration sock attached to an outer periphery of the coil and means for delivering therepeutic agents upstream of the filtration sock.
Figure 60:
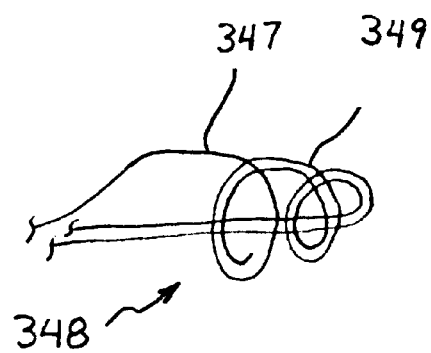
FIG. 60 is a perspective view of a core wire filament having a first portion formed of a double wire and a second portion formed of a single wire.
Figure 61:
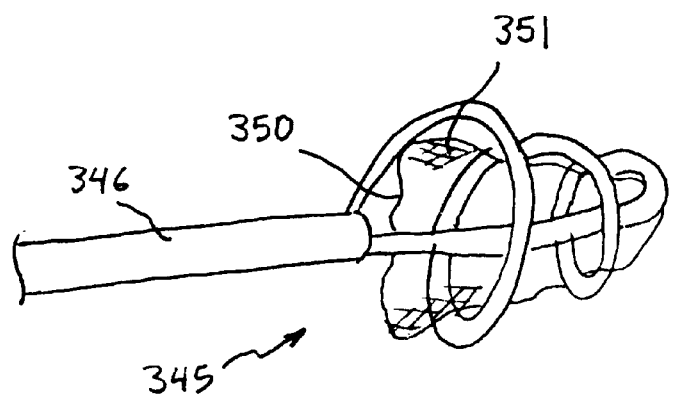
FIGS. 61, 62 and 63 are perspective views of a helical-shaped coil having a filtration sock attached to an inner periphery of the coil and a telescoping tube assembly for facilitating deployment and removal.

FIG. 59 shows another conical-shaped coil apparatus 340, which is similar to the coil apparatus 330 of FIGS. 57 and 58, except that the filtration sock 341 is attached to an outer periphery of the coiled portion 342 instead of the inner periphery. The coiled portion 342 of the apparatus, which is porous as in the above-described embodiments, is thus positioned on an upstream side of the filtration sock 341. With this construction, the therepeutic fluids will be infused primarily upstream of the filtration sock 341.

The configurations shown in FIGS. 57 to 59 are particularly suitable for infusing blood thinners, such as GP IIb/IIIa inhibitors, fibrinolytic compounds, hirudin and heparin, into the filtration sock 331, 341 and/or on the proximal side of the sock. Wetting of the sock 331, 341 with anticoagulants will serve to increase the effectiveness of the filter by reducing site induced clotting (i.e., letting the filter remove blood-entrained particulate without promoting clotting of blood due to the filter itself). Additional therapeutic agents can be introduced downstream of the filtration sock 331, 341 with or without the sock wetting. For example, a multiple lumen tubing could be used to infuse a first drug from a first lumen having holes facing the filtration sock, and a second drug from a second lumen having holes facing away from the filtration sock.

Figure 62:
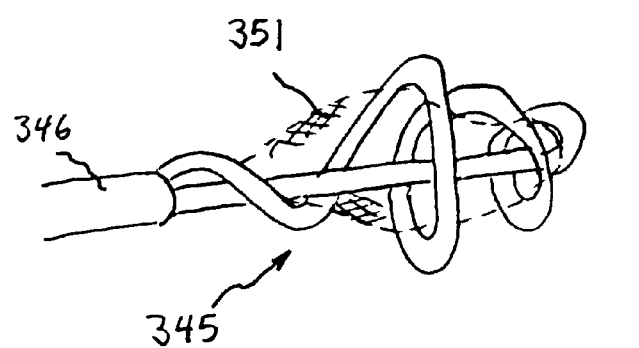
Figure 63:
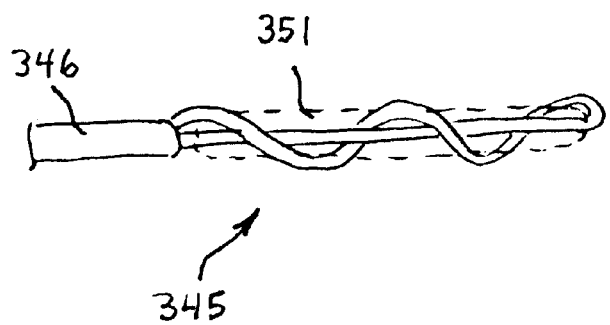

FIGS. 60 to 63 show a coil apparatus 345 which is attached to a telescoping tube 346 to facilitate deploying and removing the coil apparatus 345. The coil apparatus 345 has a first portion 347 with a shape defined by double strands of a wire filament 348, and a second portion 349 with a shape defined by a single strand of the wire filament 348. The preformed wire filament 348 is shown by itself in FIG. 60. The second portion 349 defined by the single strand of wire filament 348 is less rigid than the first portion 347 defined by the double strands of wire filament 348. As a result, when the telescoping tube 346 is retracted away from the coil apparatus 345, the second portion 349 defined by the single wire filament is deformed before the first portion 347 defined by the double wire filament, thereby closing the open end 350 of the filtration sock 351, as shown in FIG. 62. The particulate trapped by the filtration sock 351 is therefore kept within the sock 351 as the coil apparatus 345 is removed. Additional movement of the telescoping tube 346 away from the coil apparatus 345 causes the first portion 347 defined by the double wire filament to also shrink in diameter, as shown in FIG. 63, to thereby facilitate removal of the coil apparatus 345.

As an alternative to the single and double wire filament portions 347, 349 described above, a single wire filament having varying thickness or rigidity can be used to accomplish the same result. For example, a single wire filament having a thinner diameter in the coil closest to the telescoping tube 346 could be used to cause the open end of the filtration sock 351 to be closed first as the telescoping tube 346 is retracted away from the coiled portion. The varying thickness or rigidity in the wire filament can be created by chemically machining the wire filament.

Figure 64:
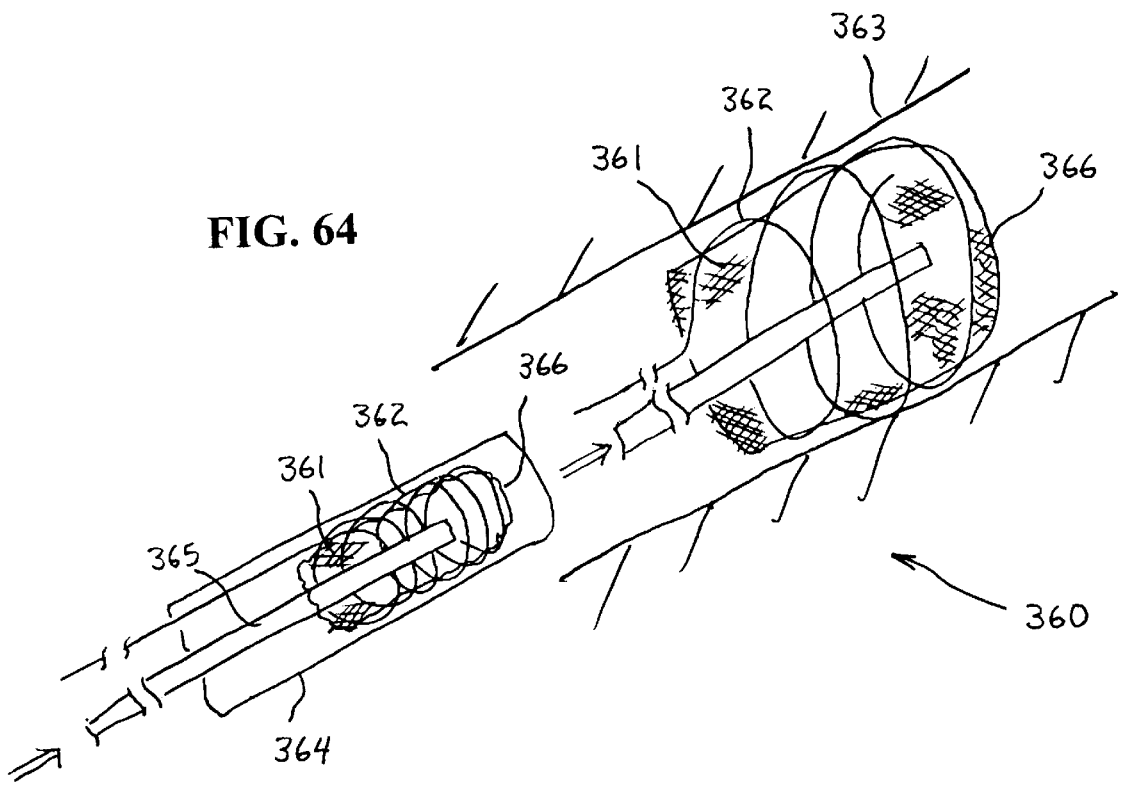
FIG. 64 is a perspective view of a coil having a filtration sock attached to an inner periphery and a push rod for pushing the coil from a deployment sheath.

FIG. 64 shows a coil apparatus 360 having a filtration sock 361 attached to an inner periphery of the coiled portion 362. The coil apparatus 360 is introduced into the vessel 363 by a deployment sheath 364, as shown on the left side of FIG. 64. The filtration sock 361 is stretched or folded to a reduced size with the coiled portion apparatus 362 to fit within the deployment sheath 364. A push rod 365 is provided for pushing the coil apparatus 360 from the deployment sheath 364. When the coil apparatus 360 is pushed out of the deployment sheath 364 and deployed within the vessel 363, the coiled portion 362 expands in diameter until it fills the diameter of the vessel 363, as shown on the right side of FIG. 64. The push rod 365 engages the closed end 366 of the filtration sock 361 to push the coil apparatus 360 out of the deployment sheath 364.

Figure 65:
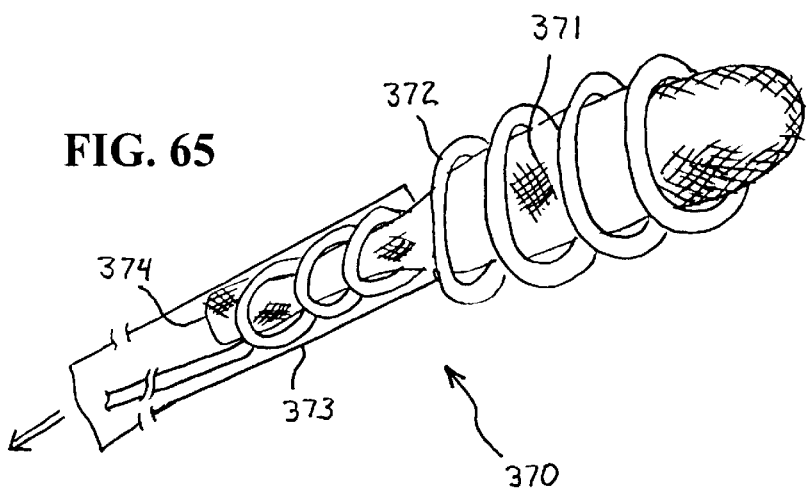
FIG. 65 is a perspective view of a coil having a filtration sock attached to an inner periphery thereof as the coil is being pulled into a sheath for removal from a vessel.

FIG. 65 shows a coil apparatus 370 having a filtration sock 371 attached to an inner periphery of the coiled portion 372, similar to the coil apparatus 360 shown in FIG. 64. The coil apparatus 370 in FIG. 65 is. shown after it has been pulled partially back into a sheath 373 for removal from a vessel after usage. In this position, the open end 374 of the filtration sock 371 has been closed by the reduced diameter of the coiled portion 372 as the coil apparatus 370 is pulled into the sheath 373. The filtration sock 371 and coil 372 initially form an elipsoid shape at the entrance to the sheath 373 and retract into the sheath 373 with the coils in an eliptical shape. The filtration sock 371 folds and collapses back into the sheath 373, thereby trapping any particulate in the sock 371 as it is retracted. The attached sock 371 keeps the coiled portion 372 from unraveling into a straight shape as the coil apparatus 370 is pulled into the sheath 373. The ratio of the diameter of the retraction sheath 373 (typically 0.086 inch inside diameter) to the polymer tube diameter from which the coil apparatus 370 of the present invention is fabricated (e.g., 0.014 inches) is sufficient to accomplish this function.

The resilient wire fiber forming the coil apparatus 370 could be chemically machined so that the portion of the resilient wire fiber forming the open end 374 of the filtration sock 371 and the first coil to enter the retraction sheath 373 is smaller and offers less resistance as it is pulled into the sheath 373. The larger stiffer wire fiber forming the rest of the coil apparatus 370 would tend to retain its shape before entering the sheath 373. The smaller wire fiber at the open end 374 of the filtration sock 371 ensures that the mouth of the sock 371 closes first as it enters the retraction sheath 373, before any entrapments in the sock 371 can be squeezed out due to deformation of the sock 371 as it is retracted.

Figure 66:
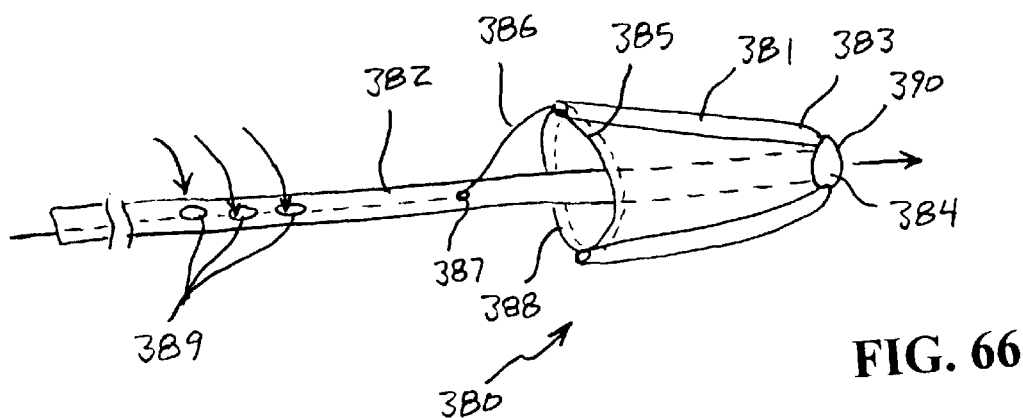
FIG. 66 is a perspective view of a filtration apparatus having a plurality of legs supporting a filtration sock, a central passage through which noncontaminated fluids can pass, and a core wire filament to aid in deployment and removal.

FIG. 66 shows a filtration apparatus 380 having a plurality of legs 381 secured to a central tube 382 in an umbrella-like configuration. Each of the legs 381 preferably comprise a resilient fiber core encased by a soft polymer tubing that adapts to the shape of the fiber core. The legs 381 are attached at first ends 383 to a distal end 384 of the central tube 382 using, for example, glue or thermal welding. A filtration sock 385 is supported by the legs 381 to form a conical or cylindrical-shaped filter that can be deployed easily and efficiently into a vessel. A core wire fiber 386 extends from a free end of the legs 381 and through a small opening 387 in a sidewall of the central tube 382 for use by an operator to aid in removal of the apparatus 380. The core wire fiber 386 preferably extends around the opening 388 of the filtration sock 385 so that the opening is 388 closed when the core wire fiber 386 is retracted by the operator for removal. The core wire fiber 386 can be made as a continuous wire fiber that extends through each of the legs 381 and also around the opening 388 of the filtration sock 385.

As in the embodiments shown in FIGS. 55 and 56, the central tube 382 has a plurality of openings 389 upstream of the filtration sock 385 into which noncontaminated fluid can pass and flow through the central tube 382 to a distal end opening 390 of the central tube 382 downstream of the filtration sock 385.

Figure 67:
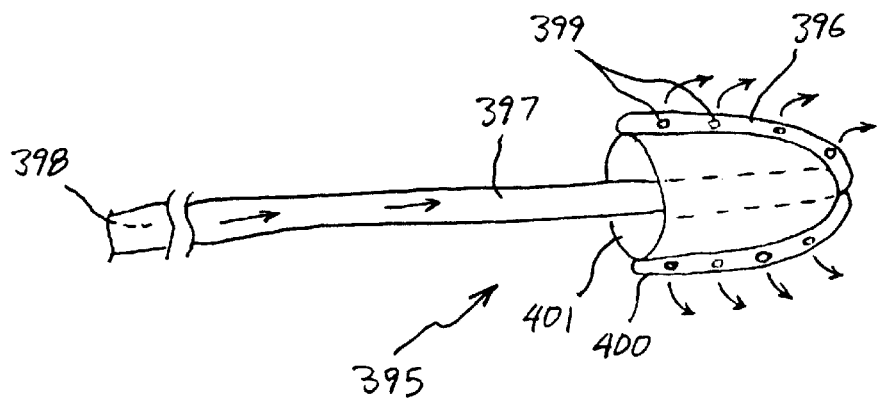
FIG. 67 is a perspective view of a filtration apparatus having a plurality of legs supporting a filtration sock, and means for infusing therapeutic agents through a plurality of openings in the legs.

FIG. 67 shows a filtration apparatus 395 having a plurality of legs 396 secured to a central tube 397 in an umbrella-like configuration, similar to the apparatus shown in FIG. 66. The filtration apparatus 395 of FIG. 67 is different from the apparatus 380 of FIG. 66 in that the legs 396 are in fluid communication with the lumen 398 of the central tube 397, and a plurality of openings 399 are provided in the polymer tubing 400 of the legs 396 to allow therapeutic fluids to be infused through the legs 396. A filtration sock 401 is supported by the legs 396 to form a conical or cylindrical-shaped filter that can be deployed easily and efficiently into a vessel.

Figure 68:
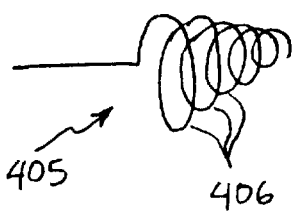
FIG. 68 is a perspective view of a helical-shaped core wire filament with closely spaced coils according to another embodiment of the invention.
Figure 69:
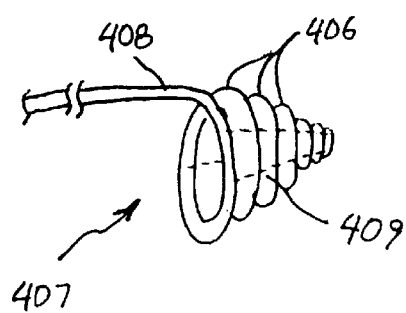
FIG. 69 is a perspective view of a helical-shaped filtration apparatus having closely spaced coils defined by the core wire filament shown in FIG. 68.

FIG. 68 shows a conical-shaped core wire filament 405 with closely spaced coils 406 that can be used to form a conical-shaped filtration apparatus 407 as shown in FIG. 69. A soft polymer tubing 408 is placed over the core wire filament 405. The portion of the polymer tubing 408 placed over the closely spaced coils 406 of the core wire filament 405 is preferably porous to form a porous coil. The touching coils 406 of the apparatus 407 are stiched together along axial seams 409 or glued together at their interface, thereby forming a uniform and compliant deformable coil apparatus 407.

Figure 70:
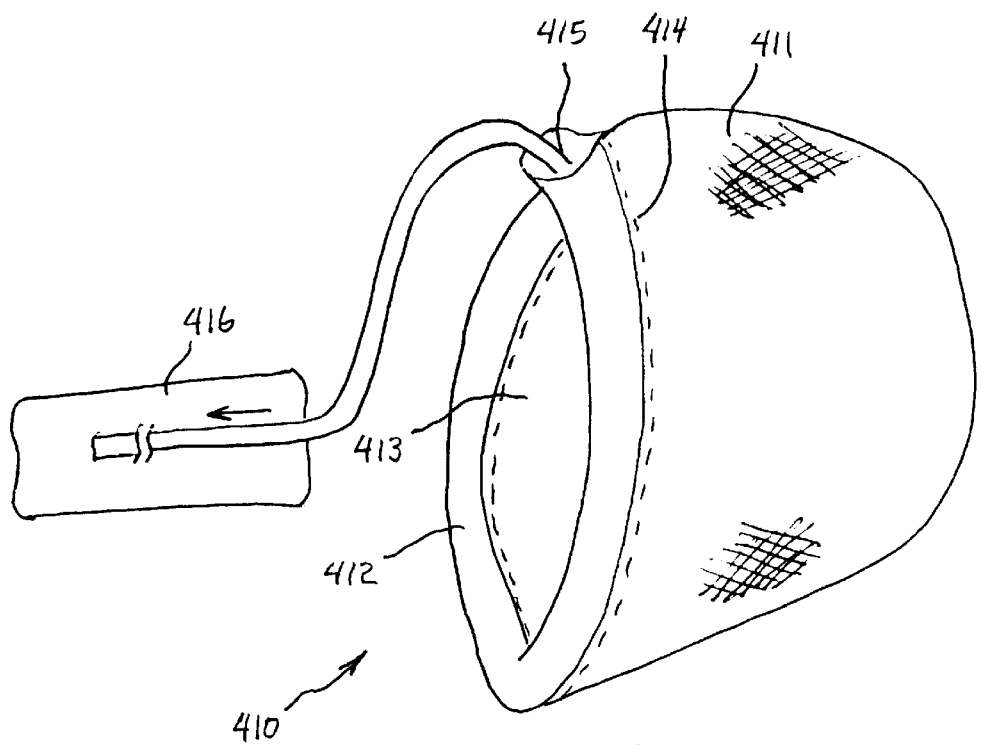
FIG. 70 is a perspective view of a coil apparatus with a filtration sock attached to the coil and being operable to close the filtration sock in the manner of a purse-string as the coil apparatus is pulled back into a sheath for removal.
Figure 71:
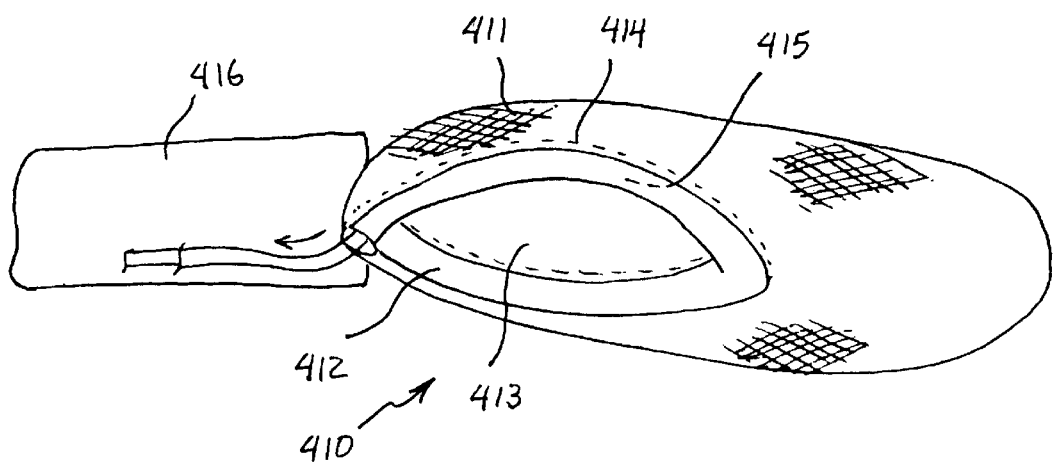
FIG. 71 is a perspective view of the coil apparatus of FIG. 70 in a partially removed position.

FIG. 70 shows a coil apparatus 410 with a filtration sock 411 attached to the coil. The filtration sock 411 has a channel 412 that extends about its open end 413 formed by stiching two layers of the filtration sock 411 together along a seam 414. The first coil 415 of the coil apparatus 410 extends through the channel 412. When the coil apparatus 410 is pulled back into a sheath 416 for removal, the first coil 415 slides out of the channel 412 in the manner of a purse-string and causes the opening 413 of the filtration sock 411 to be closed. FIG. 71 shows the coil apparatus 410 of FIG. 70 in a partially removed position with the opening 413 of the filtration sock 411 being closed by the first coil 415 being pulled out of the channel 412.

Figure 72:
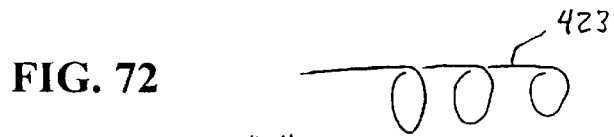
FIG. 72 is a perspective view of a core wire filament defining a plurality of axially spaced hoops and interconnecting portions between the hoops.
Figure 73:
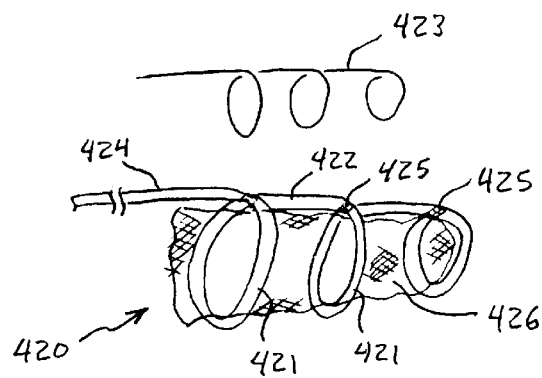
FIG. 73 is a perspective view of a filtration apparatus having a filtration sock attached to axially spaced hoops defined by the core wire filament of FIG. 72.

FIGS. 72 to 76 show a filtration apparatus 420 having a plurality of axially spaced hoops 421 interconnected by straight portions 422 that extend axially between the hoops 421. FIG. 72 shows the core wire fiber 423 used to define the shape of the filtration apparatus 420. As shown in FIG. 73, a soft polymer tubing 424 is placed over the core wire fiber 423 of FIG. 72, and the intersections 425 of the axially spaced hoops 421 are joined by a suitable bond, such as glue, wire wrapping, clamping, and so forth. A filtration sock 426 is attached to the axially spaced hoops 421 of the soft polymer tubing 424. The filtration sock 426 is attached to the tubing 424 using a suitable fastening means, such as glue, thermal welding, stitching, or the like. The portions of the polymer tubing 424 extending over the hoops 421 can be made out of porous material to allow infusion through the apparatus 420 as explained above.

Figure 74:
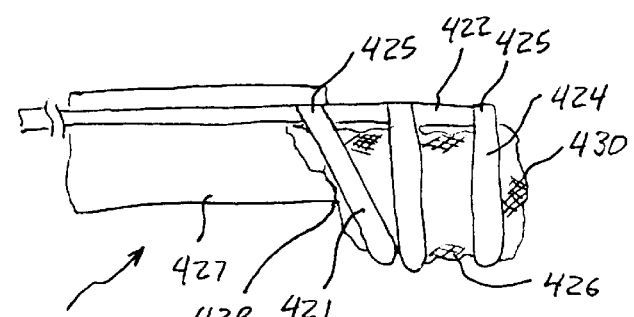
FIG. 74 is a side view of the filtration apparatus of FIG. 73 showing the apparatus being pulled into a sheath for removal.
Figure 75:
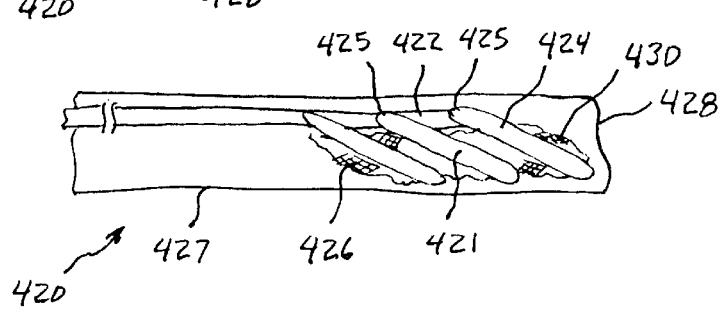
FIG. 75 is a side view of the filtration apparatus of FIG. 73 showing the apparatus having been pulled into a sheath and being ready for removal.
Figure 76:
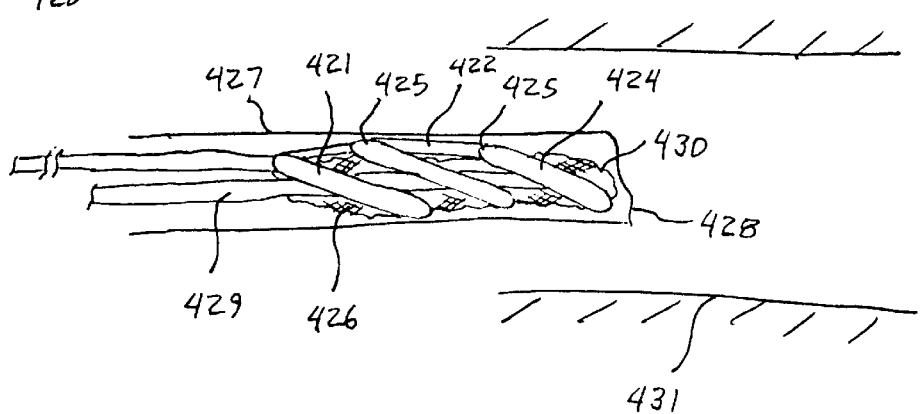
FIG. 76 is a side view of the filtration apparatus of FIG. 73 showing the apparatus contained within a sheath and a push rod to facilitate deployment.

FIG. 74 shows the filtration apparatus 420 of FIG. 73 as the apparatus is being pulled into a sheath 427 for removal. The axially spaced hoops 421 engage the opening 428 of the removal sheath 427 and are caused to fold back into a compact, folded configuration. The joined intersections 425 of the axially spaced hoops 421 facilitate a uniform and efficient folding of the filtration apparatus 420, including the filtration sock 426, as the apparatus is pulled into the sheath 427. FIG. 75 shows the filtration apparatus 420 in its folded configuration after being pulled completely into the removal sheath 427. FIG. 76 shows the filtration apparatus 420 in a deployment sheath with a push rod 429 extending through the hoops 421 and into engagement with the closed end 430 of the filtration sock 426 to facilitate deployment in a vessel 431 in the manner explained above.

Figure 77:
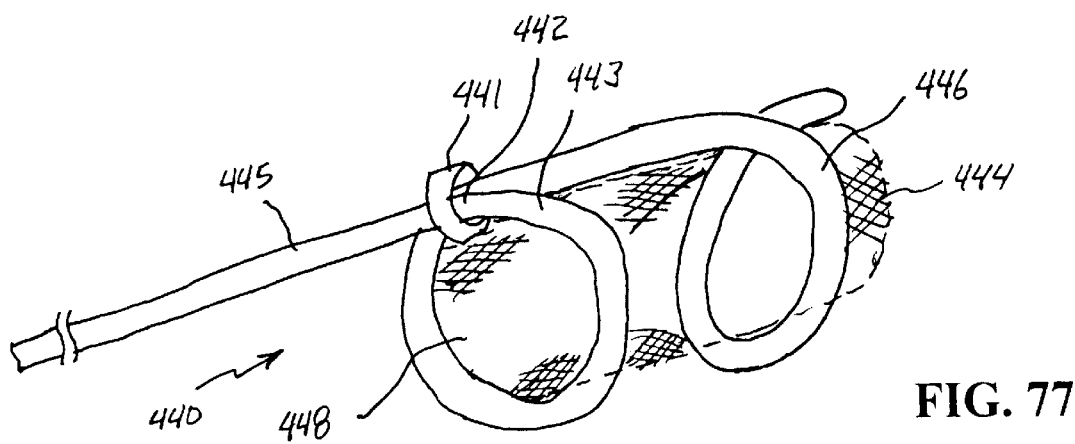
FIG. 77 is a perspective view of another filtration apparatus similar to the apparatus of FIG. 73, with a slip ring provided at the intersection of the first hoop to facilitate closing the filtration sock as the apparatus is removed.
Figure 78:
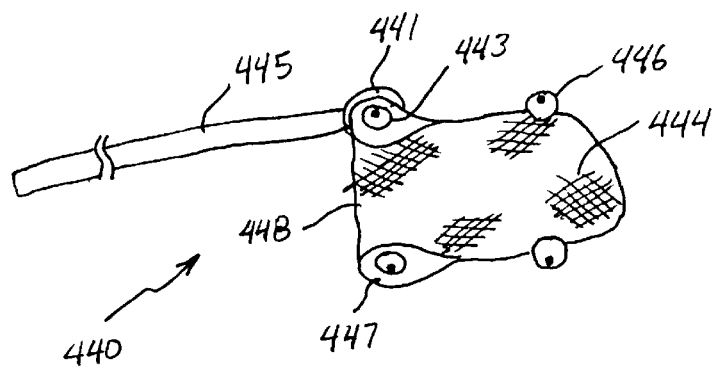
FIG. 78 is a sectional view of the filtration apparatus of FIG. 77.
Figure 79:
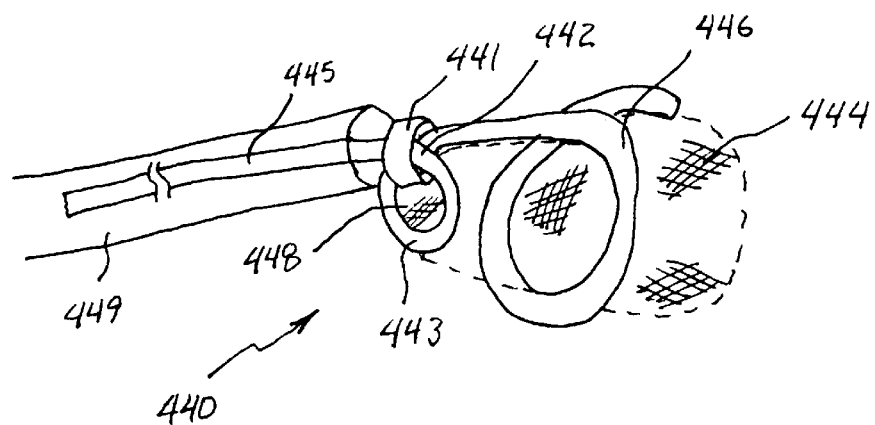
FIG. 79 is a perspective view of the filtration apparatus of FIG. 77 showing the operation of the slip ring to close the filtration sock as the apparatus is pulled into a sheath for removal.

FIGS. 77 to 79 show another filtration apparatus 440 similar to the apparatus 420 of FIG. 73, with a slip ring 441 provided at the intersection 442 of the first hoop 443 to facilitate closing the filtration sock 444 as the apparatus 440 is removed. A soft polymer tubing 445 is placed over a preformed core wire fiber, and the intersection 442 of the first hoop 443 is joined by the slip ring 441 to allow the polymer tubing 445 to slide through the slip ring 441 and change the diameter of the first hoop 443. The filtration sock 444 is attached to the axially spaced hoops 443, 446 of the soft polymer tubing 445. The filtration sock 444 is attached to the first hoop 443 of the tubing 445 using a channel 447 sewn into the open end 448 of the filtration sock 444 through which the polymer tubing 445 is inserted. The filtration sock 444 is attached to the other hoops 446 of the tubing 445 by a suitable fastening means, such as glue, thermal welding, stitching, or the like. The portions of the polymer tubing 445 extending over the hoops 443, 446 can be made out of porous material to allow infusion through the apparatus 440 as explained above.

As shown in FIG. 79, the slip ring 441 causes the filtration sock 444 to be closed as the apparatus 440 is pulled into a sheath 449 for removal. This serves to close the open end 448 of the filtration sock 444 first as the apparatus 440 enters the removal sheath 449, before any entrapments in the sock 444 can be squeezed out due to deformation of the sock 444 as it is retracted.

Figure 80:
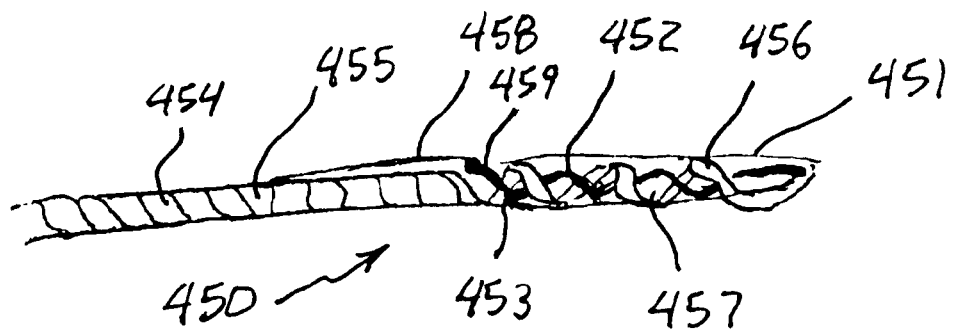
FIGS. 80 and 81 are perspective views of a filtration apparatus having a spring guide with loosely spaced coils into which a filtration sock and coil apparatus can be tucked during deployment.
Figure 81:
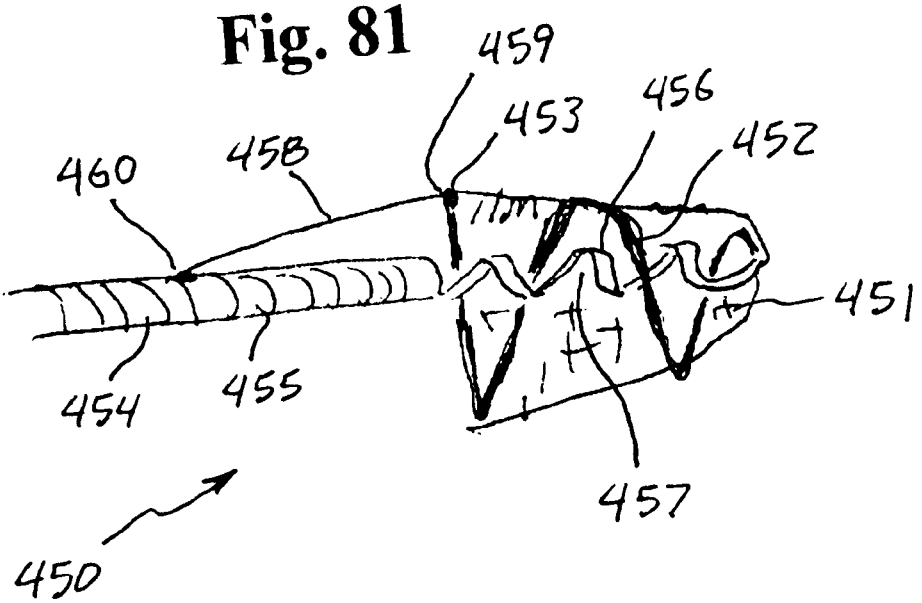

FIGS. 80 and 81 show another filtration apparatus 450 having a filtration sock 451 attached to a coil apparatus 452. The coil apparatus 452 has a preformed resilient fiber core and a polymer tubing 453 placed over the fiber core 458, as explained above. The coil apparatus 452 is connected to or integral with a distal end of a spring guide 454. The spring guide 454 is formed by a coiled spring with closely spaced coils 455 along a first portion of its length, and loosely spaced coils 456 along a distal portion of its length. The loosely spaced coils 456 at the distal portion are separated such that the coil apparatus 450 can be tucked into the spaces 457 between the coils 456 of the spring guide. 454 for deployment. The fiber core 458 of the coil apparatus 450 extends from the free end 459 of the polymer tubing 453 and passes back into a small opening 460 in the sidewall of the spring guide 454. By retracting the fiber core 458 through the spring guide 454, an operater can cause the coil apparatus 450 and filtration sock 451 to tuck into the spaces 457 between the coils 456 of the spring guide 454 to facilitate deployment and removal of the filtration apparatus 450.

The disclosed embodiments of the present invention provide apparatuses of various shapes and configurations that can be wrapped into a much smaller configuration without permanently deforming the apparatus so that it will spring back to its original configuration. The limiting factor of how small a coil or other shape can be made is the thickness of the element to be coiled or bent. For instance, a 0.25" diameter metallic steel heat-tempered spring alloy wire must be wound around a very large radius (several feet) to keep from permanently deforming, while a very thin diameter (e.g., 0.001") spring alloy wire can be wound around a very small radius (0.010") without being permanently set.

Use of "dead" soft polymer tube will follow the coil or other shape of the core element without hindering recovery of the core element to its original size during deployment. The preferred Shore D hardness of the polymer selected for the polymer tube is approximately 40, whereby any permanent set in the polymer itself due to coiling will not hinder the coil's recovery.

Use of holes, pores, or a soluble coating around the entire periphery of the apparatus prevents thrombus from forming and allows for ease of manufacturing. The size of the resilient fiber core can be tailored to make the springiness of the core variable so that the device produces a very small force on the vessel wall while still maintaining enough force to recover its shape during deployment.

The polymer tube can be tailored to reduce the pressure exerted by the apparatus on the artery wall. The configuration of the embodiments of the present invention allow for positive and accurate deployment of the apparatus through existing devices and prevents the apparatus from dragging through the vessel during deployment.

As used in this application, the terms "diagnostic," "therapeutic" and "fluid-based" agents encompass any diagnostic compound, such as dyes for markers, as well as any therapeutic compound that has a desired pharmacologic effect in a particular subject. For example, the therapeutic agent can be an anticoagulant, such as D-Phe-Pro-Arg chloromethyl ketone, an RGD peptide-containing compound, heparin, antithrombin compounds, platelet receptor antagonists, antithrombin antibodies, antiplatelet receptor antibodies, aspirin, protagladin inhibitors, platelet inhibitors, or tick antiplatelet peptide. The therapeutic agent could also be a promoter of vascular cell growth, such as a growth factor promotor, growth factor receptor agonist, transcriptional activator, translational promoter, or endothelia cells. Alternatively, the therapeutic agent can be an inhibitor of vascular cell growth, such as a growth factor inhibitor, growth factor receptor antagonist, transcriptional repressor, translational repressor, antisense DNA, antisense RNA, replication inhibitor, inhibitory antibodies, antibodies directed against growth factors, bifunctional molecules consisting of a growth factor and a cytotoxin, and bifunctional molecules consisting of an antibody and a cytotoxin. In addition, the therapeutic agent could be a cholesterol-lowering agent, a vasodilating agent, and agents that interfere with endogenous vasoactive mechanisms. The therapeutic agent could also be a radioactive material used in intravascular radiotherapy.

While the present invention has been disclosed primarily in connection with treating coronary artery disease, the invention may also be used for treatment of various other body organs, including the biliary ducts, or the genital-uretal organs. The term vessel, as used in this application, encompasses any duct, canal, tube or other cavity that contains or conveys a body fluid.

It will be appreciated that the present invention is not limited to the exact construction or method steps that have been described above and illustrated in the accompanying drawings, and that various modifications and changes can be made without departing from the scope of the invention. It is intended that the scope of the invention only be limited by the appended claims.

We claim:

1. An apparatus for filtering fluids intravascularly, comprising:
    a resilient fiber core having a preset shape;
    a polymer material covering the resilient fiber core and having a shape defined by the preset shape of the resilient fiber core; and
    a filtering device attached to said polymer material for filtering fluids;
        wherein said filtering device comprises a filtration sock made of a porous material, said filtration sock having an open end and a closed end, said open end being held open by the preset shape of the resilient fiber core.

2. The apparatus according to claim 1, wherein said preset shape of said resilient fiber core is such that said resilient fiber core defines a general outline of a cylindrical-shaped coil, and said filtering device comprises a filtration sock attached to said polymer material with an open end at one end of said cylindrical-shaped coil and a closed end at another end of said cylindrical-shaped coil.

3. The apparatus according to claim 1, wherein said preset shape of the resilient fiber core includes a plurality of hoops connected together by linear portions extending in an axial direction, said polymer material covers the hoops and linear portions to define a plurality of axially spaced hoops, and said filtering device comprises a filtration sock attached to said polymer material with an open end attached to at least one of said hoops and a closed end for filtering fluids.

4. The apparatus according to claim 1, wherein a portion of said polymer tubing covering said resilient fiber core is constructed from a braided, stitched, or other porous material for releasing fluid-based agents from said apparatus.

5. The apparatus according to claim 1, wherein said preset shape of the resilient fiber core is conical with a large end and a small end, and said filtering device comprises a filtration sock attached to said polymer material with an open end adjacent the large end of said conical shape and a closed end adjacent the small end of said conical shape.

6. The apparatus according to claim 1, wherein said preset shape of the resilient fiber core defines a plurality of legs extending from a central tube, and said filtering device comprises a filtration sock supported in an umbrella-like configuration by said legs with an open end of said filtration sock adjacent to free ends of said legs.

7. The apparatus according to claim 1, further comprising a central tube to which said resilient fiber core is attached, and said central tube comprises an open lumen, a means for allowing fluids to pass into said lumen at an upstream location from said filtering device, and a means for allowing fluids to flow through said lumen to a location downstream of said filtering device to bypass said filtering device.

8. The apparatus according to claim 1, wherein at least a portion of an outer surface of said polymer tubing is covered by a soluble coating containing a therapeutic agent.

9. The apparatus according to claim 1, wherein said filtering device comprises a filtration sock with a channel formed at an open end thereof for receiving at least a first coil of said resilient fiber core and the polymer material covering said resilient fiber core, said resilient fiber core having a resiliency such that said open end of said filtration sock is closed in a purse-string manner upon pulling said resilient fiber core through said channel.

10. The apparatus according to claim 1, further comprising an inner support tube attached to a first end of said resilient fiber core and an outer support tube attached to a second end of said resilient fiber core, said inner and outer support tubes being concentric and movable relative to each other to selectively close an open end of said filtering device.

11. The apparatus according to claim 1, wherein said preset shape of the resilient fiber core includes a plurality of hoops connected together by linear portions extending in an axial direction, said polymer material covers the hoops and linear portions to define a plurality of axially spaced hoops, said filtering device comprises a filtration sock attached to said polymer material with an open end attached to a first one of said hoops and a closed end for filtering fluids, and a slip ring connecting an intersection of one of said linear portions and said first hoop to facilitate closing said filtration sock upon pulling said apparatus into a sheath for removal.

12. An apparatus for filtering fluids intravascularly comprising:
   a resilient fiber core having a preset shape;
   a polymer material covering the resilient fiber core and having a shape defined by the preset shape of the resilient fiber core; and
   a filtering device attached to said polymer material for filtering fluids;
      wherein said polymer tubing comprises a means for delivering and infusing a fluid-based therapeutic agent into a vessel adjacent to said filtering device.

13. A method for filtering fluids intravascularly, comprising the steps of:
   providing an apparatus having a resilient fiber core with a preset shape, a soft polymer tubing encasing the resilient fiber core and adapting to the shape of the resilient fiber core, and a filtering device attached to said polymer tubing for filtering fluids;
   placing said apparatus into a vessel; and
   causing a diameter of said filtering device to enlarge within the vessel.

14. The method according to claim 13, further comprising the steps of:
   loading said apparatus into a delivery sheath having an internal diameter smaller than a preset diameter of the preset shape of said resilient fiber core;
   inserting said delivery sheath and said apparatus into a vessel; and
   moving said apparatus out of said delivery sheath whereby said resilient fiber core causes said apparatus and said filtering device to increase in diameter and lodge within the vessel.

15. The method according to claim 13, wherein the step of providing an apparatus comprises providing a coil-shaped apparatus having a coiled portion having first and second ends, said second end being connected to an outer support tube, said outer support tubes being movable relative to said first end in a telescoping manner; and
   further comprising the step of moving said outer support tube relative to said first end to change a diameter of the coiled portion within the vessel.

16. A coil apparatus for filtering fluids intravascularly, comprising:
   a resilient fiber core having a linear portion and a coiled portion;
   a polymer tubing encasing the resilient fiber core and adapting to the shape of the resilient fiber core, said polymer tubing comprising a first portion encasing the linear portion of the resilient fiber core and a second portion encasing the coiled portion of the resilient fiber core; and
   a filtering device attached to said second portion of said polymer tubing for filtering fluids.

17. The coil apparatus according to claim 16, wherein said filtering device comprises a filtration sock made of a porous material, said filtration sock having an open end and a closed end, said open end being held open by the coiled portion of the resilient fiber core.

18. The coil apparatus according to claim 16, wherein said polymer tubing has a lumen and a means for releasing fluid-based agents delivered through said lumen.

19. An apparatus for filtering fluids intravascularly, comprising:
   a resilient fiber core having a preset shape;
   a polymer material covering the resilient fiber core and having a shape defined by the preset shape of the resilient fiber core; and
   a filtering device attached to said polymer material for filtering fluids;
      wherein said polymer material has a lumen and a means for releasing fluid-based agents delivered through said lumen.

* * * * *